(12) United States Patent
Ueno et al.

(10) Patent No.: US 7,067,631 B2
(45) Date of Patent: Jun. 27, 2006

(54) FUSED DNA SEQUENCE, FUSED PROTEIN EXPRESSED FROM SAID FUSED DNA SEQUENCE AND METHOD FOR EXPRESSING SAID FUSED PROTEIN

(75) Inventors: Eiichi Ueno, Tokyo (JP); Noboyuki Fujii, Tokyo (JP); Masahisa Okada, Tokyo (JP)

(73) Assignee: Fujirebio Inc. (Fujirebio Kabushiki Kaisha), Tokyo (JP)

( * ) Notice: Subject to any disclaimer, the term of this patent is extended or adjusted under 35 U.S.C. 154(b) by 527 days.

(21) Appl. No.: 10/457,372

(22) Filed: Jun. 10, 2003

(65) Prior Publication Data

US 2004/0018534 A1    Jan. 29, 2004

Related U.S. Application Data

(62) Division of application No. 08/778,717, filed on Dec. 27, 1996, now Pat. No. 6,602,689.

(30) Foreign Application Priority Data

Dec. 28, 1995  (JP) .................................. 7-352225

(51) Int. Cl.
*C07K 14/195*   (2006.01)
*C07K 14/435*   (2006.01)
*C12P 21/04*    (2006.01)
*C12N 9/12*     (2006.01)

(52) U.S. Cl. ...................... 530/350; 435/69.7; 435/194
(58) Field of Classification Search ...................... None
See application file for complete search history.

(56) References Cited

U.S. PATENT DOCUMENTS 4,797,359 A * 1/1989 Finkelstein ................. 435/69.1
5,723,588 A * 3/1998 Donofrio et al. ........... 530/350
6,280,998 B1 * 8/2001 Mathur et al. ........... 435/252.3

FOREIGN PATENT DOCUMENTS

WO    WO 87/05935    10/1987

OTHER PUBLICATIONS

Darimont et al., The EMBO Journal, 13(3):1772-1781, 1994.*
Andreas Heltzel et al., Journal of Bacteriology, vol. 176, No. 15, pp. 4790-4793, Aug. 1994, "Cloning, Expression, and Molecular Characterization of the Gene Encoding an Extrmely Thermostable [4Fe-4S] Ferredoxin from the Hyperthermophilic Archaeon Pyrococcus Furiosus".
Thomas Kath, et al, Archives of Biochemistry and Biophysics, vol. 307, No. 02, pp 405-410, Dec. 1993, "Identification, Cloning, and Expression of the Gene for Adenylate Kinase from the Thermoacidophilic Archaebacterium Sulfolobus Acidocaldarius".
M. Moracci, et al., Carbohydrate Bioengineering, pp 77-84, 1995, "Properties and Production of the B-Glycosidase from the Thermophilic Archaeon Sulfolobus Solfataricus Expressed in Mesophilic Hosts".
Parsons, J.A. et al. " Peptide Hormones", published by University Park Press (Baltimore), see Rudinger et al. Chapter 1, pp. 1-6.
Lazar et al. Mol. Cell Biol. 8(3):1247, Mar. 1988.
Burgess et al. J. Cell Biol. 111:2129, Nov. 1990.
Smith et al. Gene 67:31, Jul. 1988.

* cited by examiner

*Primary Examiner*—Marianne P. Allen
(74) *Attorney, Agent, or Firm*—Oblon, Spivak, McClelland, Maier & Neustadt, P.C.

(57) ABSTRACT

Disclosed are a fused DNA sequence which comprises a DNA sequence of a heat-resistant protein, fused directly or indirectly to a DNA sequence coding a selected protein or peptide, a fused protein expressed from the fused DNA sequence, and a method for expressing the fused protein.

5 Claims, 12 Drawing Sheets

FUSED DNA SEQUENCE, FUSED PROTEIN EXPRESSED FROM SAID FUSED DNA SEQUENCE AND METHOD FOR EXPRESSING SAID FUSED PROTEIN

This application is a divisional of U.S. application Ser. No. 08/778,717, filed on Dec. 27, 1996, now issued as U.S. Pat. No. 6,602,689.

BACKGROUND OF THE INVENTION

This invention relates to expression of a fused protein, more specifically to a fused DNA sequence including a DNA sequence coding a heat-resistant protein, a fused protein expressed by said fused DNA sequence, and a method for expressing said fused protein.

Progress in genetic engineering has enabled analysis of a protein which has been purified from a natural substance, at a genetic level and artificial amplification of a desired protein (Itakura et al., Science, vol. 198, p. 1056 (1977)). By application of a DNA sequence to which thioredoxin (hereinafter referred to as "TRX" in the specification) (International Provisional Patent Publication No. 507209/1993) or glutathione-S-transferase (hereinafter referred to as "GST" in the specification) (International Provisional Patent Publication No. 503441/1989) which has been invented thereafter is fused, even a protein which is inherently expressed with difficulty can be expressed, and a technique of expressing a fused protein has been used widely.

TRX and GST can be applied to fusion and expression of various proteins which are expressed with difficulty, but even in GST which has been essentially used for the purpose of expressing a soluble fused protein, a fused protein becomes insoluble depending on a protein to be fused so that productivity is lowered, or a fused protein to which TRX is fused may have a problem that a nonspecific reaction is liable to occur. Therefore, it has been desired to provide a fused protein having further excellent operatability and productivity.

SUMMARY OF THE INVENTION

Thus, an object of the present invention is to provide a novel fused DNA sequence having excellent operatability and productivity for expressing a desired protein or peptide, a fused protein expressed from said fused DNA sequence, and a method for expressing the fused protein using said fused DNA sequence.

The present inventors have studied intensively in order to solve the problems in the art and consequently found that when a DNA sequence coding a selected protein or peptide and a DNA sequence coding a heat-resistant protein are fused directly or indirectly and a fused protein is expressed from the resulting fused DNA sequence, the productivity of the desired protein or peptide is raised, and said fused protein~has heat resistance to make a purification step simple and easy, to accomplish the present invention.

That is, the present invention relates to a fused DNA sequence comprising a DNA sequence coding a heat-resistant protein or peptide, fused directly or indirectly to a DNA sequence coding a selected protein or peptide, a fused protein expressed by said fused DNA sequence, and a method for expressing the fused protein using said DNA sequence.

The fused protein of the present invention has high solubility and can maintain even heat resistance derived from heat-resistant protein genes. Because of such a characteristic of the fused protein, when the fused protein is purified, unnecessary substances can be removed simply and easily by heat treatment so that the fused protein can be obtained with good yield.

In the case of TRX derived from *Escherichia coli* and GST derived from *Schistosoma japonicum,* which have been widely used as a fused protein, *Escherichia coli* and *Schistosoma japonicum* can live in bodies of mammals and other creatures so that when a fused protein using TRX or GST is used as an antigen of an immunoreaction, a nonspecific reaction due to *Escherichia coli* or *Schistosoma japonicum* might be caused. To the contrary, the great characteristic of the fused protein of the present invention resides in that a heat-resistant protein derived from a thermophilic bacterium which cannot live in living bodies of mammals and other creatures is used so that even when the fused protein of the present invention is used as an antigen of an immunoreaction, a nonspecific reaction derived from the fused protein is caused with difficulty.

DESCRIPTION OF THE PREFERRED EMBODIMENTS

Figure 1:
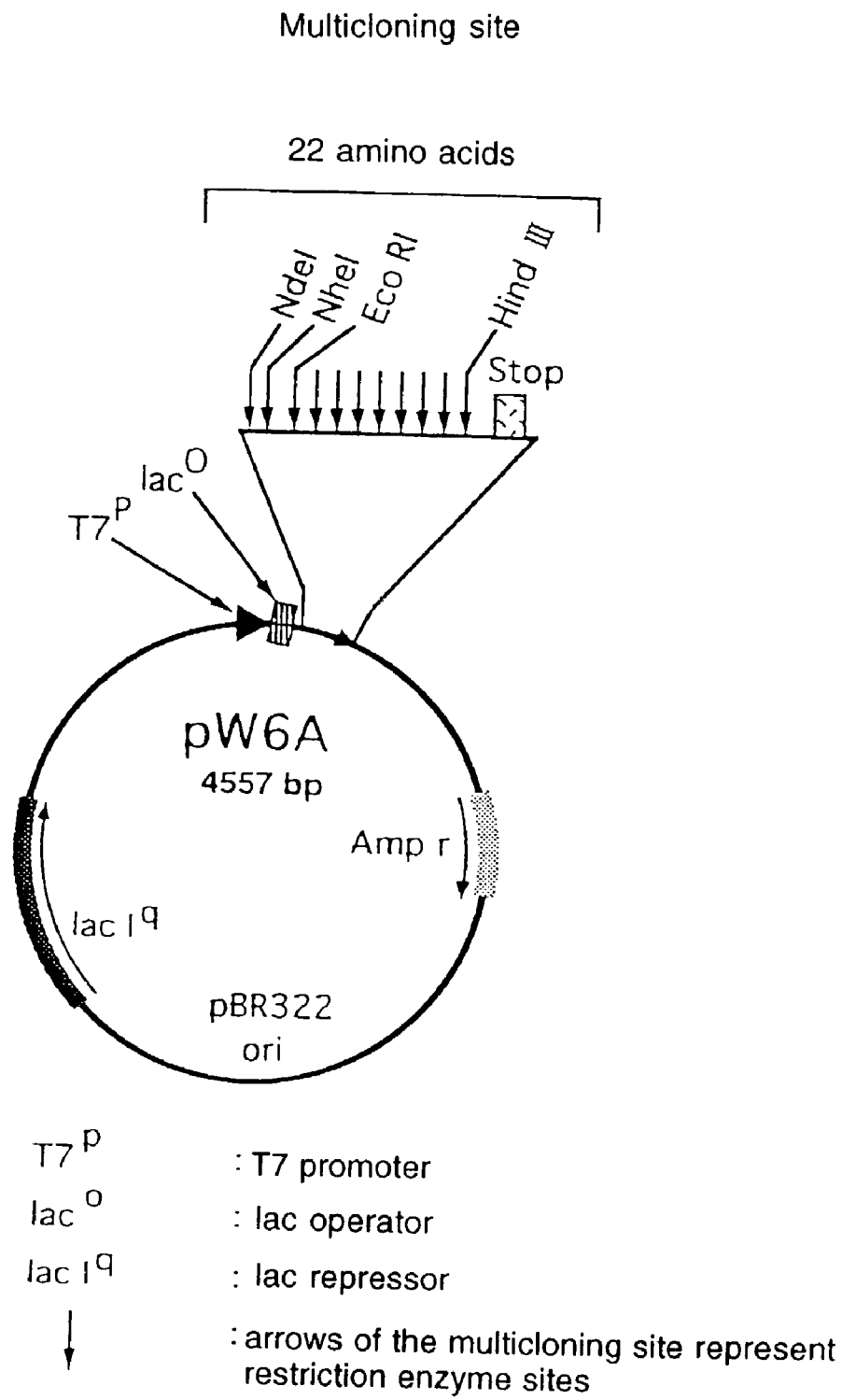
FIG. 1 is a detailed view of an expression vector pW6A.

In the following, the present invention is explained in detail.

The DNA sequence coding a heat-resistant protein of the present invention means a DNA sequence coding a protein which is not thermally denatured even at 55° C. or higher, preferably 75° C. or higher. As a specific phenomenon of thermal denaturation, there may be mentioned inactivation or insolubilization of a protein. As the DNA sequence coding a protein which is not thermally denatured at 55° C. or higher, there may be mentioned, for example, a DNA sequence possessed by a thermophilic bacterium which can live at 55° C. or higher. From the properties of an expressed protein and easiness of post-treatment, it is preferred to use a DNA sequence possessed by the so-called highly thermophilic bacterium which can live at 75° C. or higher. As the highly thermophilic bacterium, there may be mentioned, for example, *Thermophilus, Sulfolobus, Pyrococcus, Thermotoga, Pyrobaculum, Pyrodictium, Thermococcus, Thermodiscus, Metanothermus* and *Metanococcus* (FEMS. MICRO.

BIOL. REV., Vol. 75, pp. 117–124 (1990), ANU. REV. MICROBIOL., Vol. 47, pp. 627–653 (1993)). As the heat-resistant protein, there may be mentioned, for example, adenyl kinase derived from a *Sulfolobus* bacterium (*Sulfolobus acidocaldalius* Adenylate kinase: Arch. Biochem. Biophys., Vol. 207, pp. 405–410 (1993)) (hereinafter referred to as "AK" in the specification), DNA polymerase derived from a *Thermophilus* bacterium, ferredoxin derived from a *Pyrococcus* bacterium (*Pyrococcus furiosus* Ferredoxin: Biochemistry, Vol. 31, pp. 1192–1196 (1992)) (hereinafter referred to as "FDX" in the specification), glucosidase derived from *Pyrococcus furiosus* bacterium (*Pyrococcus furiosus* Glucosidase), rubredoxin derived from *Pyrococcus Furiosus* bacterium (*Pyrococcus furiosus* Rubredoxin: Biochemistry, Vol. 30, pp. 10885–10895 (1991)), glutamate dehydrogenase derived from *Pyrococcus Furiosus* bacterium (*Pyrococcus furiosus* Glutamate dehydrogenase: Gene, Vol. 132, pp. 189–197 (1988)), glyceraldehyde phosphate dehydrogenase derived from *Metanothermus fervids* bacterium (*Metanothermus fervids* Glyceraldehyde 3-phosphate dehydrogenase: Gene, Vol. 64, p. 189–197 (1988)), glutamate synthetase derived from *Metanococcus volate* bacterium (*Metanococcus volate* Glutamate synthetase: Res. Microbiol., Vol. 140, pp. 355–371 (1989)), L-lactate dehydrogenase derived from *Thermotoga maritina* bacterium (*Thermotoga maritina* L-lactate dehydrogenase: Eur. J. Biochem., Vol. 216, pp. 709–715 (1993)) and elongation factor derived from *Thermococcus celer* bacterium (*Thermococcus celer* Elongation Factor I-alpha: Nucleic acid res. Vol. 18, p. 3989 (1990)), but the heat-resistant protein coded by the DNA sequence of the present invention is not limited thereby. DNA coding the heat-resistant protein of the present invention can be purified from these highly thermophilic bacteria, but it can be also synthesized based on a known DNA sequence. For synthesis of DNA of the heat-resistant protein, a known technique such as β-cyano-ethylphosphoamidite method (Sinha et al., Nucleic Acids Bos., Vol. 12, p. 4539 (1984)) and a method described in Letsinger, R. L. et al., J. Am. Chem. Soc., vol. 88, p. 5319 (1966) may be suitably used. In Examples each of which is an embodiment of the present invention, DNA's of FDX derived from *Pyrocuccus* bacterium and AK derived from *Sulfolobus* bacterium having amino acid sequences shown in SEQ ID NO: 1 and 3, respectively, are synthesized by the β-cyano-ethylphosphoamidite method. DNA sequences synthesized are shown in SEQ ID NO: 2 and 4, respectively.

The DNA sequence coding a selected desired protein or peptide of the present invention is not limited to a particular DNA sequence. Any DNA sequence can be used so long as it is a DNA sequence coding a protein or peptide which is desired to be expressed as a fused protein. The present invention is particularly useful when a necessary expression amount of a selected desired protein or peptide can be obtained with difficulty by DNA itself coding said protein or peptide.

The fused DNA sequence of the present invention can be fused by using a known method such as a ligation method and a linker ligation method. When fusion is carried out, the DNA sequence of a selected desired protein or peptide and the DNA sequence of the heat-resistant protein may be fused directly or may be fused indirectly, if necessary. In the case of indirect fusion, a linker sequence is inserted between the DNA sequence coding a desired protein or peptide and the DNA sequence coding the heat-resistant protein. As said linker sequence, there can be used a sequence coding a polypeptide for bonding a desired protein or peptide and the heat-resistant protein to each other and a sequence coding a polypeptide which can be cleaved or digested selectively by a known chemical method or enzymatic method. When the linker sequence is inserted between the DNA sequence coding a desired protein or peptide and the DNA sequence coding the heat-resistant protein, only a selected desired protein or peptide portion can be also purified by, after the fused protein is expressed, cleaving or digesting the linker sequence by using a chemical means such as bromocyan or an enzymatic means such as thrombin or a factor Xa.

In order to express the fused protein of the present invention, a common technique of genetic engineering can be used. For example, the fused DNA sequence of the present invention is inserted into a vector which is suitable for expression, said vector is introduced into a culture host, and expression of the fused protein is induced. After the host is grown by culture or the like, sonication of the host and purification such as a column operation are carried out to obtain a desired fused protein or peptide. Host cells to be used may be any cells such as bacterial cells, eucaryotic cells and mammal cells so long as they are cells which can express a foreign protein or peptide, and there may be mentioned, for example, *Escherichia coli*, yeast, *Bacillus subtilis*, Baculo virus and COS cells.

The fused protein of the present invention may be used-as such as a fused protein, or a desired protein or peptide portion thereof obtained by separation and purification may be used.

EXAMPLES

The present invention is described in detail by referring to Reference examples and Examples.

Example 1

Preparation of FDX-Expressing Vector pWF6A

Figure 2:
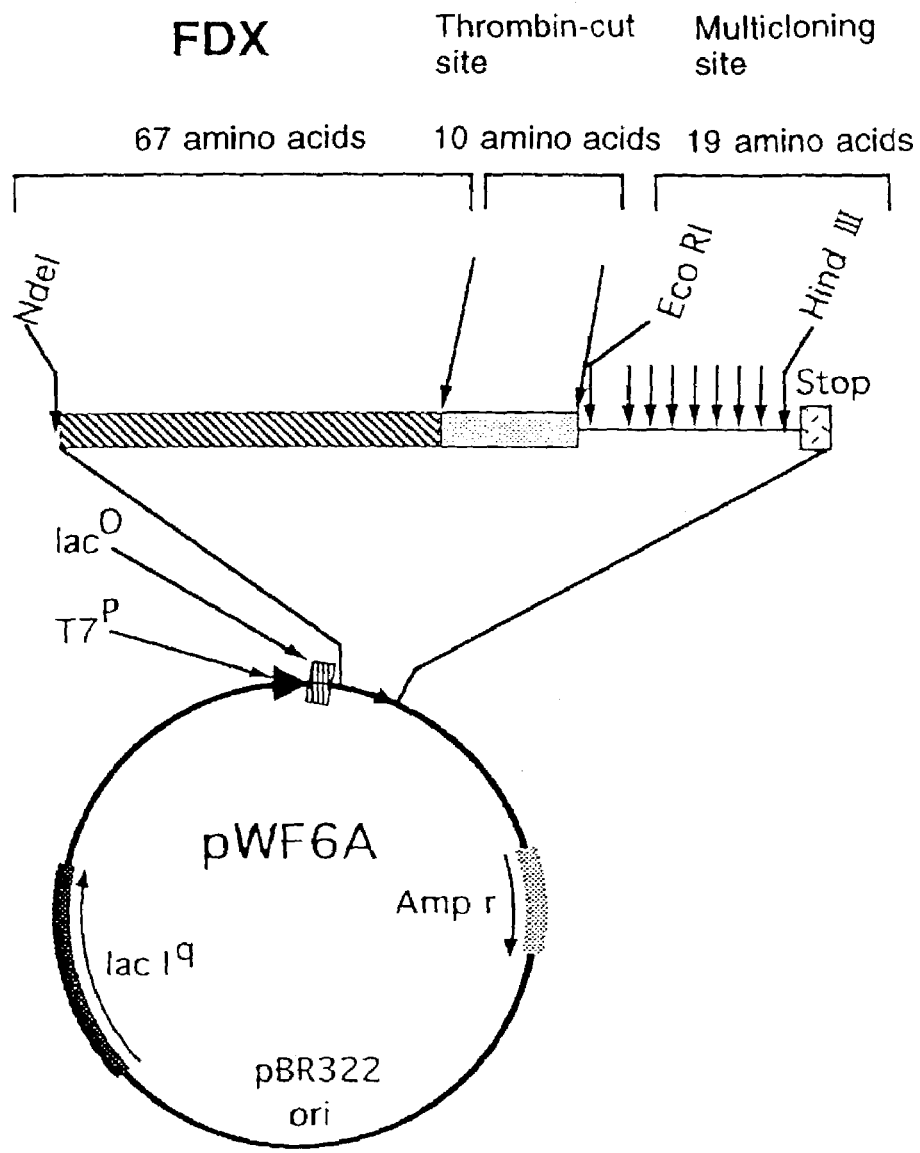
FIG. 2 is a detailed view of an expression vector pWF6A.

By using 8 primers of 53 mer prepared based on a known DNA sequence of *Pyrococcus furiosus* FDX by using a DNA synthesizer (Model 392, trade name, manufactured by PERKIN ELMER Co.), genes of *Pyrococcus furiosus* FDX were synthesized by the assemble PCR (polymerase chain reaction) method. In the assemble PCR method, a Taq polymerase (produced by Toyobo Co.) was used, and the total base number of 248 bp was amplified under conditions of 30 cycles of 94° C.-1 minute, 55° C.-1 minute and 72° C.-1 minute. A NdeI site was added to 5'-end, a restriction enzyme EcoRI was added to 3'-end, and a thrombin-cut site was added to C terminal. This fragment was integrated into the NdeI and EcoRI sites of 4.6 Kb of a pW6A vector prepared from pGEMEX-1 (trade name, produced by Promega Co.) and pGEX-2T (trade name, produced by Pharmacia Biotec Co.) to prepare pWF6A as a vector expressing FDX. A detailed view of pW6A is shown in FIG. 1, and a detailed view of pWF6A is shown in FIG. 2. pWF6A contains, at the NdeI and EcoRI sites, genes of a fused protein comprising 96 amino acids including 67 amino acids derived from FDX, 10 amino acids derived from a thrombin-cleaved site and 19 amino acids derived from multi cloning site of pW6A. The base sequence of the inserted fragment was confirmed by a DNA sequence kit (trade name: Sequenase kit Ver. 2.0, produced by Amersham United States Biochemical Co.). DNA sequence of the FDX inserted into pW6A and amino acids sequence coded by said sequence are shown in SEQ ID NO: 1 and SEQ ID NO: 2, respectively, and DNA sequence of the pW6A is shown in SEQ ID NO: 5. In the sequence table, ATG of the restriction enzyme site NdeI is shown as 1 and sequences up to the stop codon of a multi-cloning site are shown. The expression "***" in the amino acid sequence means the stop codon. pWF6A was introduced into host *Escherichia coli* and then cultured for 2 hours in a medium (hereinafter referred to as "the LB medium" in the specification) containing 1% of bactotryptone, 0.5% of yeast extract, 1% of sodium chloride and 50 μg/ml of ampicillin and having pH 7.5. Thereafter, 1 mM isopropyl thio-galactopyranoside (hereinafter referred to as "IPTG" in the specification) was added thereto, and the mixture was cultured for 2 hours to induce expression. 10 mM Tris-hydrochloride having pH 7.5 and 1 mM ethylenediaminetetraacetic acid (hereinafter abbreviated to as "EDTA" in the specification) (in the following, this buffer is referred to as "a TE buffer" in the specification) were added to the precipitates of *Escherichia coli,* the precipitates were sonicated, and 15% sodium dodecylsulfate-polyacrylamide gel electrophoresis (hereinafter referred to as "SDS-PAGE") according to the Laemmli method was carried out. By Coomassie brilliant blue staining (hereinafter referred to as "CBB staining" in the specification), a band was confirmed at about 22 Kda, and FDX of *Pyrococcus furiosus* forming a dimer was recognized.

Example 2

Purification of FDX pWF6A prepared in Example 1 was introduced into host *Escherichia coli* and then cultured under conditions of using the LB medium at 37° C. By preculture, a concentration of *Escherichia coli* in a culture broth was made to have such turbidity that absorbance at a wavelength of 600 nm was about 1.0, 1 mM IPTG was added thereto to induce expression. After the mixture was cultured for 3 hours, centrifugation was carried out to recover *Escherichia coli.* 200 ml of a 50 mM Tris-hydrochloride buffer (hereinafter referred to as "the Tris buffer" in the specification) having pH 8.0 was added to recovered *Escherichia coli,* followed by sonication treatment under ice cooling. After centrifugation, the expressed fused protein was recovered in the supernatant as a soluble component. When this supernatant was subjected heat treatment at 85° C. for 15 minutes, about 80% of the *Escherichia coli* protein was thermally denatured and precipitated, and 90% or more of FDX was recovered in the centrifugation supernatant after the heat treatment.

This supernatant was purified by ion exchange using a QFF anion exchange column (trade name, manufactured by Pharmacia Biotec Co.) equilibrated with the Tris buffer. When the supernatant was eluted by a column equilibrated buffer containing sodium chloride, FDX was recovered at a concentration of about 0.3 M sodium chloride-eluted fraction. Then, this FDX fraction was purified by using a RESOURCE RPC column (trade name, manufactured by Pharmacia Biotec Co.) equilibrated with 20 mM sodium hydroxide. When the fraction was eluted by acetonitrile, purified FDX was recovered at a concentration of about 10% acetonitrile-eluted fraction.

Reference Example 1

Purification of TRX pWT8A prepared as a vector expressing TRX in the same manner as in pWF6A prepared in Example 1 was introduced into host *Escherichia coli* and then cultured under conditions of using the LB medium at 37° C. After the same induction of expression as in Example 1 was carried out, *Escherichia coli* was recovered by centrifugation. An osmotic shock was given to recovered *Escherichia coli,* and TRX existing at a periplasmic fraction was extracted. Extracted TRX was subjected to first purification by using a RESOURCE RPC column (trade name, manufactured by Pharmacia Biotec Co.) equilibrated with 20 mM sodium hydroxide. When TRX was eluted by acetonitrile, TRX was recovered at a concentration of about 10% to 20% acetonitrile-eluted fraction. Recovered TRX was dialyzed to 4 M guanidine hydrochloride and then subjected to second purification by using the reverse phase column under the same conditions. Similarly as in the first purification, purified TRX was recovered at a concentration of about 10% to 20% acetonitrile-eluted fraction.

Example 3

Specificity Test of FDX and TRX by the Western Blotting Method

An anti-*Escherichia coli* antibody was supposed as a non-specific reaction substance, and the reactivities of FDX purified in Example 2 and TRX purified in Reference example 1 were examined.

A SDS-solubilized material of *Escherichia coli* DH5α, a supernatant of *Escherichia coli* DH5α sonicated and a SDS-solubilized material of *Escherichia coli* to which a pW50 vector (made by Fuji Rebio) was introduced were used as immunogen and immunized to 3 rabbits to prepare the total 9 kinds of the respective anti-*Escherichia coli* rabbit serums. FDX purified in Example 2 and TRX purified in Reference example 1 were subjected to SDS-PAGE according to the Laemmli method and then transferred to nitrocellulose membranes. After blocking the protein portion adsorbed to the nitrocellulose membranes with 1% skim milk dissolved in PBS, the western blotting method was carried out by using the above 9 kinds of the anti-*Escherichia coli* rabbit serums diluted 500 times, respectively, as primary anti-bodies, and using a peroxidase (hereinafter referred to as "POD" in the specification)-labeled anti-rabbit antibody as a secondary antibody. For coloring, 4-chloro-1-naphthol and hydrogen peroxide were used. At the portion corresponding to the molecular weight of FDX, no substance reacting with the anti-*Escherichia coli* rabbit antibody was confirmed, but at the portion corresponding to the molecular weight of TRX, among 9 kinds of the anti-*Escherichia coli* rabbit serums, 6 kinds of the serums in which the supernatant of *Escherichia coli* DH5α sonicated and the SDS-solubilized material of *Escherichia coli* into which the pW50 vector was introduced were used as immunogen were reacted, respectively.

In the same manner as described above, the western blotting method was carried out by 25 samples of human specimen HTLV-T/II mix panel 204 serums (trade name, produced by Boston Biomedica Co.) diluted 50 times, respectively, as primary antibodies, and using POD-labelled anti-human IgG as a secondary antibody. Reactivities at sites where FDX was transferred was not confirmed, but the reactions of 2 samples among 25 samples at sites where TRX was transferred were confirmed. The results are shown in Table 1.

TABLE 1

| Specimen No. | Intensity of reaction (+, −) by western blotting | |
|---|---|---|
| | FDX | TRX |
| PRP-204-01 | − | − |
| PRP-204-02 | − | − |
| PRP-204-03 | − | − |
| PRP-204-04 | − | − |
| PRP-204-05 | − | − |
| PRP-204-06 | − | − |
| PRP-204-07 | − | − |
| PRP-204-08 | − | − |
| PRP-204-09 | − | − |
| PRP-204-10 | − | − |
| PRP-204-11 | − | − |
| PRP-204-12 | − | + |
| PRP-204-13 | − | − |
| PRP-204-14 | − | − |
| PRP-204-15 | − | − |
| PRP-204-16 | − | − |
| PRP-204-17 | − | − |
| PRP-204-18 | − | − |
| PRP-204-19 | − | − |
| PRP-204-20 | − | − |
| PRP-204-21 | − | − |
| PRP-204-22 | − | − |
| PRP-204-23 | − | + |
| PRP-204-24 | − | − |
| PRP-204-25 | − | − |

+: positive, −: negative

Example 4

Specificity Test of FDX and TRX by the ELISA Method Using Human Specimens

On ELISA plates (produced by Becton Deckinson Co.) were sensitized each 50 μl of 25 μg/ml of FDX purified in Example 2 and TRX purified in Reference example 1, respectively.

Figure 3:
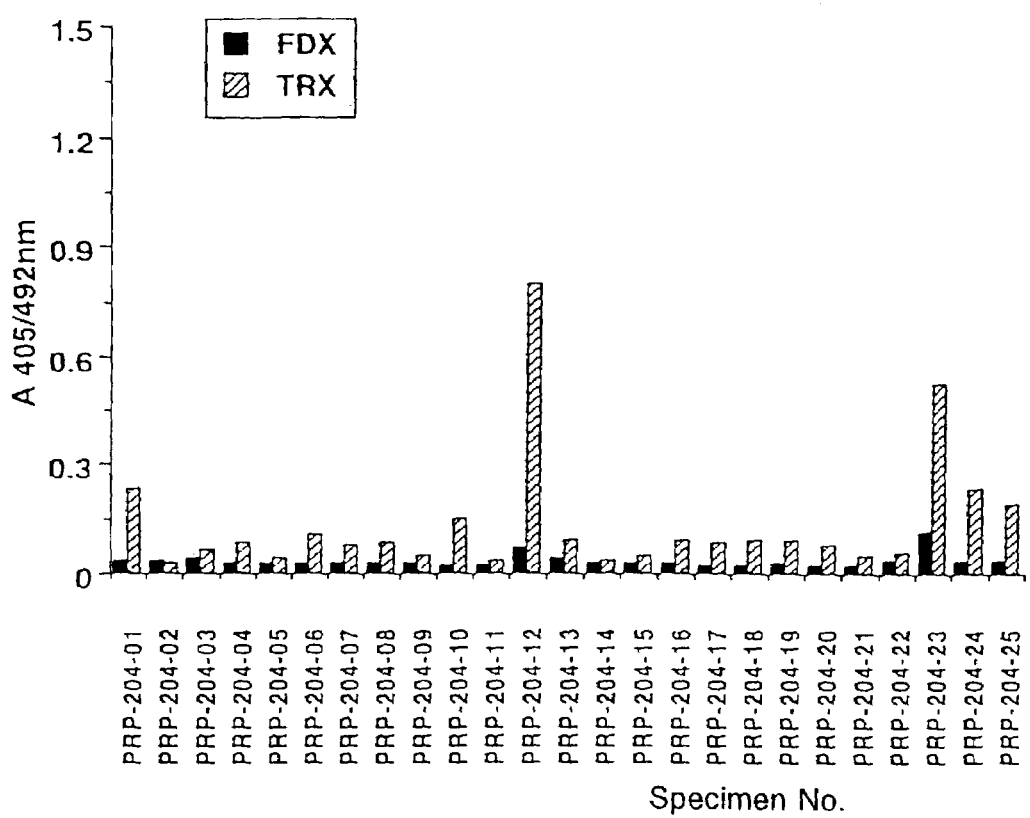
FIG. 3 is a graph showing the reactivity of a fused protein and a negative specimen.

After blocking the protein portion adsorbed onto wells of the ELISA plate with 1% skim milk, a specificity test according to the ELISA method was carried out by using the human specimens produced by Boston Biomedica Co. diluted 500 times used in Example 3 as primary antibodies and POD-labelled anti-human IgG as a secondary antibody. For coloring, ABTS and hydrogen peroxide were used. The measurement results were shown by difference between absorbances at a wavelength of 405 nm and a wavelength of 492 nm (difference between absorbances was described as A405/492 nm). In the reactions with the specimens, whereas there was no specimen exceeding twice of a blank in the case of FDX, the specimens exceeding twice of a blank were confirmed in 6 samples among 25 samples in the case of TRX. FDX derived from *Pyrococcus furiosus* was different from TRX derived from *Escherichia coli* in that neither nonspecific reaction nor cross reaction derived from *Escherichia coli* was recognized. The results are shown in FIG. 3.

Example 5

Expression of FDX-fused HTLV-I p19-fused protein and FDX-fused HTLV-II p19-fused protein From infected cell lines expressing HTLV-I and HTLV-II, genomic DNA was extracted by the method of Molecular Cloning by J. Sambrook et al. Next, by using a primer to which EcoRI and BamHI sites were added, the PCR method was carried out in the same manner as in Example 1 to obtain about 400 bp of p19DNA fragments in the respective gag regions. These fragments were integrated into pWF6A to prepare pWFIP19 as a vector expressing p19 of HTLV-I and pWFIIP19 as a vector expressing p19 of HTLV-II. DNA sequences of the FDX-fused HTLV-I p19 and FDX-fused HTLV-II p19 each of which is inserted into the vectors are shown in SEQ ID NO: 6 and 8, respectively, and amino acids sequences coded by said DNA sequences are shown in SEQ ID NO: 7 and 9, respectively. In the same manner as in Example 1, these vectors were introduced into *Escherichia coli*, and expression of the respective fused proteins was induced. Samples for electrophoresis were prepared under the same conditions as in Example 1. After subjecting to 12.5% SDS-PAGE according to the Laemmli method, one sheet of gel was subjected to CBB staining, and the other sheet was transferred to nitrocellulose membranes by the method shown in Example 3. By using an anti-native HTLV-I p19 monoclonal antibody (a GIN-7 antibody, Tanaka, Y. et al., Gann., Vol. 74, pp. 327 to 330 (1983)) or an anti-native HTLV-II p19 monoclonal antibody as a primary antibody, and a POD-labeled anti-mouse IgG as a secondary antibody, these were reacted with the fused proteins by the same method as in Example 3 and coloring was carried out by using 4-chloro-1-naphthol and hydrogen peroxide, expression of the fused proteins reacting with the respective monoclonal antibodies corresponding to the respective fused proteins was recognized. These fused proteins gave a band at about 34 Kda which was the same position as that of the CBB-stained gels. The expression amounts of the FDX-fused HTLV-I p19 antigen and the FDX-fused HTLV-II p19 antigen were increased by several hundreds times as compared with the case where the p19 antigen of HTLV-I and the p19 antigen of HTLV-II were expressed directly.

Example 6

Expression of FDX-fused HTLV-I p20E(gp21)-fused Protein and HTLV-II p20E(gp21)-fused Protein By the same method as in Example 5, by using DNA of cells infected with HTLV-I and HTLV-II, about 500 bp of p20E(gp21) DNA fragments in the respective env regions were obtained by the PCR method. These DNA fragments were integrated into EcoRI and BamHI of pWF6A prepared in Example 1 to prepare pWFIE1 as a vector expressing p20E of HTLV-I and pWFIIE10 as a vector expressing p20E of HTLV-II. DNA sequences of the FDX-fused HTLV-I p20E and FDX-fused HTLV-II p20E each of which is inserted into the vectors are shown in SEQ ID NO: 10 and 12, respectively, and amino acids sequences coded by said DNA sequences are shown in SEQ ID NO: 11 and 13, respectively. These vectors were introduced into *Escherichia coli*, and expression of a FDX-fused HTLV-I p20E-fused protein (hereinafter referred to as "FDX-20(I)" in the specification) and a FDX-fused HTLV-II p20E-fused protein (hereinafter referred to as "FDX-20(II)" in the specification) was induced under the same conditions as in Example 1. In the same manner as in Example 1, *Escherichia coli* was sonicated. After subjecting to 12.5% SDS-PAGE according to the Laemmli method, one sheet of gel was subjected to CBB staining, and the other sheet was transferred to nitrocellulose membranes at 120 mA for 3 hours. After blocking the protein portion adsorbed to the nitrocellulose membranes with a phosphate buffer containing 1% of BSA (bovine serum albumin), 1 µg/ml of an anti-p20E(gp21) monoclonal antibody (F-10, Sugamura, K. et al., J. Immunol., Vol. 132, pp. 3180 to 3184 (1984)) reacting with p20E(gp21) antigens of native HTLV-I and HTLV-II was reacted with the fused proteins at room temperature for 1 hour, and then reacted with a POD-labeled anti-mouse IgG at room temperature for 1 hour. Subsequently, when coloring was carried out by using 4-chloro-1-naphthol and hydrogen peroxide, expression of fused proteins reacting with the anti-p20E(gp21) monoclonal antibody corresponding to the respective fused proteins was recognized. These fused proteins gave a band at about 32 Kda which was the same position as that of the CBB-stained gels.

The expression amounts of FDX-20(I) and FDX-20(II) were increased by several hundreds times as compared with the case where p20E of HTLV-I and p20E of HTLV-II were expressed directly.

Example 7

Purification of FDX-20(I)- and FDX-20(II)-fused Proteins

PWFIE1 and pWFIIE10 prepared in Example 6 were introduced into host *Escherichia coli*, respectively, and then cultured under conditions of using the LB medium at 37° C. By preculture, a concentration of *Escherichia coli* in culture broths was made to have such turbidity that absorbance at a wavelength of 600 nm was about 1.0, 1 mM IPTG was added thereto to induce expression. Three hours after IPTG was added, centrifugation was carried out to recover *Escherichia coli*. 200 ml of a 50 mM Tris-hydrochloride buffer containing 1% Triton×100 (trade name, produced by Rohm & Haas Co.) and 2 M urea with pH 8.0 was added to recovered *Escherichia coli*, followed by sonication treatment under ice cooling. Centrifugation was carried out to recover insoluble materials (inclusion bodies). The inclusion bodies were solubilized by using a 4 M guanidine hydrochloride-10 mM dithiothreitol (hereinafter referred to as "DTT" in the specification) solution. The solubilized bodies were purified by a RESOURCE RPC column (trade name, manufactured by Pharmacia Biotec Co.) equilibrated with 20% acetonitrile and 20 mM sodium hydroxide. When the bodies were eluted by acetonitrile, purified FDX-20(I)- and FDX-20(II)-fused proteins were recovered at a concentration of about 30 to 40% acetonitrile-eluted fractions, respectively. Reference Example 2 Purification of TRX-fused HTLV-I p20E-fused protein and TRX-fused HTLV-II p20E-fused protein In the same manner as in Example 6, p20E(gp21) in an env region of HTLV-I or HTLV-II was introduced into the TRX-expressing vector pWT8A prepared in Reference example 1 to prepare pWTIE1 and pWTIIE10, followed by expression. In the same manner as in Example 7, by the purification method using a RESOURCE RPC column (trade name, manufactured by Pharmacia Biotec Co.), a TRX-fused HTLV-I p20E-fused protein (hereinafter referred to as "TRX-20(I)" in the specification) and a TRX-fused HTLV-II p20E-fused protein (hereinafter referred to as "TRX-20(II)" in the specification) were purified.

Example 8

Reactivity Test of Fused Proteins (1) Test by the Western Blotting Method

By using FDX-20(I) and FDX-20(II) purified in Example 7 and TRX-20(I) and TRX-20(II) purified in Reference example 2, reactivities with human HTLV specimens in the western blotting method were compared.

In the same manner as in Example 3, the western blotting method was carried out by using the human specimen HTLV-I/II mix panel produced by Boston Biomedica Co. diluted 50 times as primary antibodies and POD-labelled human IgG as a secondary antibody. FDX-20(I) and FDX-20(II), and TRX-20(I) and TRX-20(II) were reacted with the same specimens, respectively. The results are shown in Table 2.

TABLE 2

| Specimen No. | Intensity of reaction (+, −) by western blotting | | | |
|---|---|---|---|---|
| | FDX-20 (I) | TRX-20 (I) | FDX-20 (II) | TRX-20 (II) |
| PRP-204-01 | + | + | + | + |
| PRP-204-02 | − | − | − | − |
| PRP-204-03 | + | + | + | + |
| PRP-204-04 | − | − | + | + |
| PRP-204-05 | + | + | − | − |
| PRP-204-06 | − | − | − | + |
| PRP-204-07 | + | + | + | + |
| PRP-204-08 | − | − | − | − |
| PRP-204-09 | + | + | − | − |
| PRP-204-10 | + | + | + | + |
| PRP-204-11 | + | + | + | + |
| PRP-204-12 | ++ | ++ | ++ | ++ |
| PRP-204-13 | + | + | + | + |
| PRP-204-14 | − | − | + | + |
| PRP-204-15 | + | + | + | + |
| PRP-204-16 | − | − | + | + |
| PRP-204-17 | + | + | + | + |
| PRP-204-18 | + | + | + | + |
| PRP-204-19 | + | + | − | − |
| PRP-204-20 | − | − | − | − |
| PRP-204-21 | + | + | + | + |
| PRP-204-22 | + | + | + | + |
| PRP-204-23 | + | + | + | + |
| PRP-204-24 | + | + | + | + |
| PRP-204-25 | + | + | + | + |

+: positive, ++: strongly positive, −: negative (2) Comparison by the ELISA Method On ELISA plates (produced by Becton Deckinson Co.) were sensitized each 50 µl of FDX-20(I) and FDX-20(II) purified in Example 7 and TRX-20(I) and TRX-20(II) purified in Reference example 2 at a concentration of 3 µg/ml, respectively.

Figure 4:
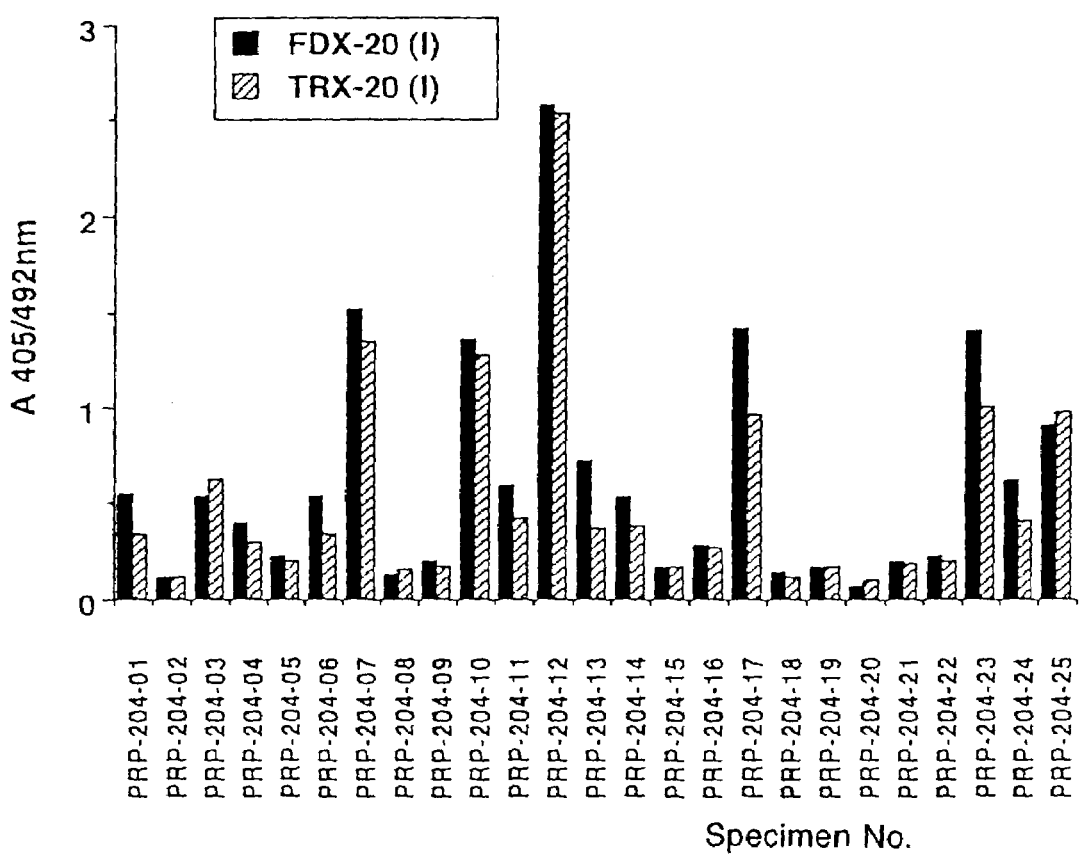
FIG. 4 is a graph showing the reactivity of a HTLV-I-fused protein and a positive specimen.
Figure 5:
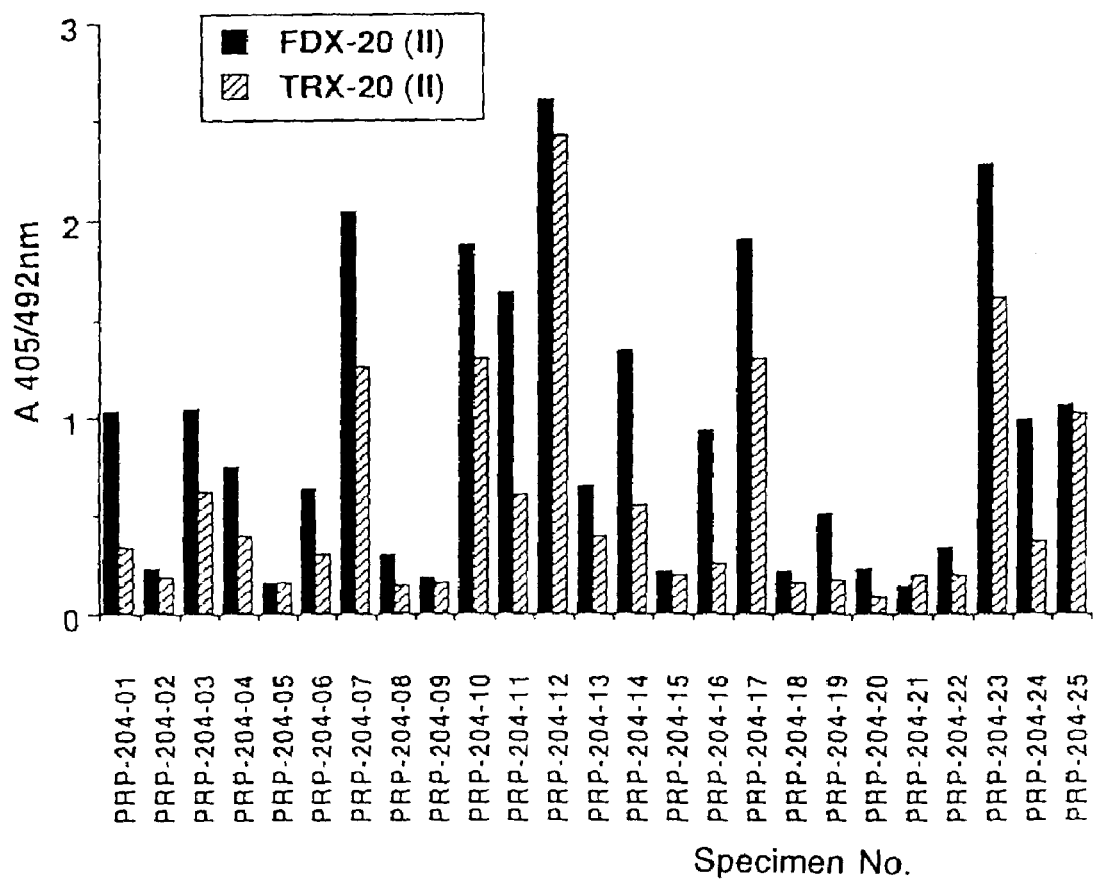
FIG. 5 is a graph showing the reactivity of a HTLV-II-fused protein and a positive specimen.

The ELISA method was carried out by using these ELISA plates and using the human specimens produced by Boston Biomedica Co. diluted 500 times as primary antibodies and POD-labelled anti-human IgG as a secondary antibody in the same manner as in Example 4. FDX-20(I) and FDX-20 (II), and TRX-20(I) and TRX-20(II) were reacted with the same specimens. The results are shown in FIG. 4 and FIG. 5.

(3) Test of Dependency on Concentration by the ELISA Method

In order to examine reactivities to the anti-p20E(gp21) monoclonal antibody and a negative serum, 10 µg/ml to ½ dilution series of FDX-20(I) and FDX-20(II) purified in Example 7 and TRX-20(I) and TRX-20(II) purified in Reference example 2 were prepared, respectively, and ELISA plates (produced by Becton Deckinson Co.) were sensitized with each 50 µl thereof.

Figure 6:
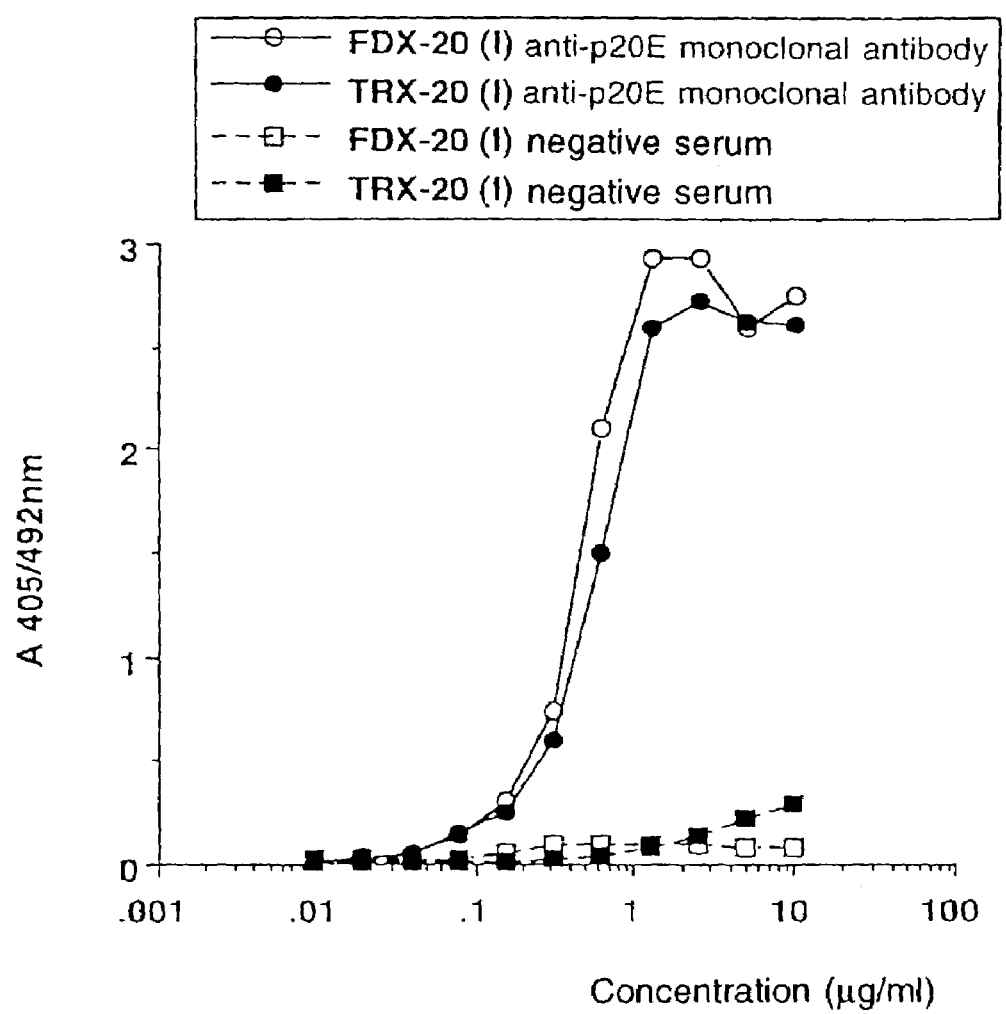
FIG. 6 is a graph showing the reactivity depending on concentration of a HTLV-I-fused protein.
Figure 7:
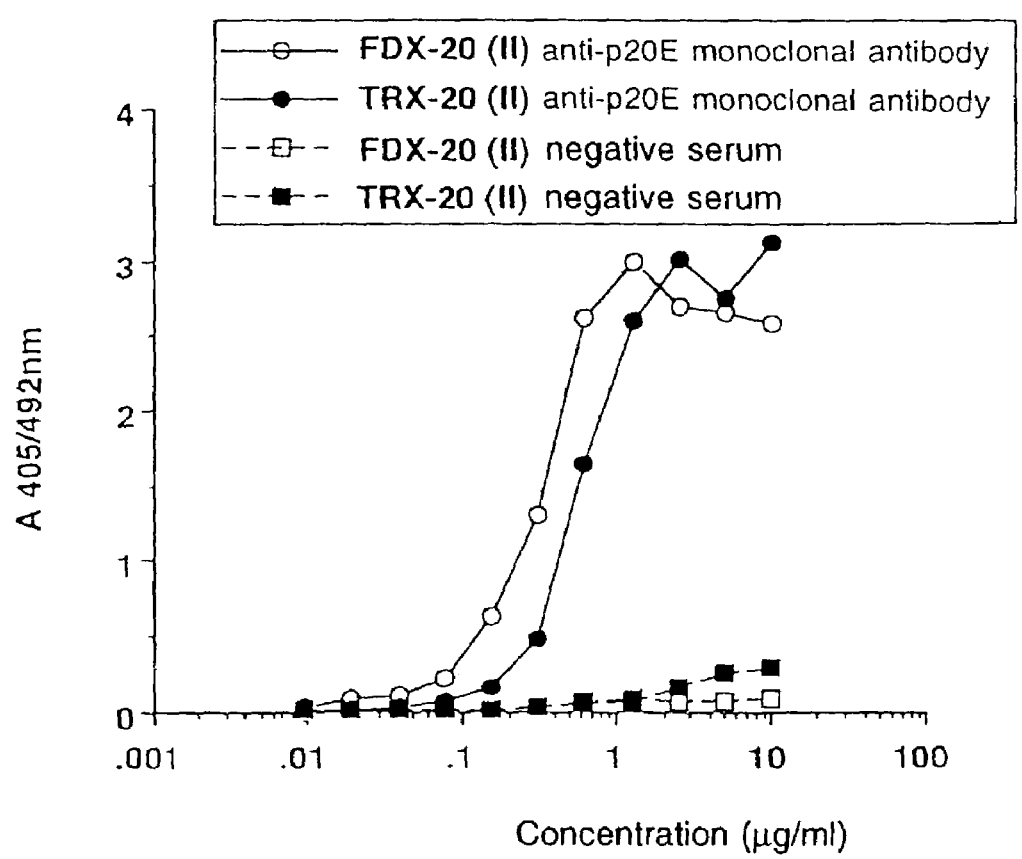
FIG. 7 is a graph showing the reactivity depending on concentration of a HTLV-II-fused protein.

The ELISA method was carried out by using these ELISA plates and using the anti-p20E(gp21) monoclonal antibody diluted 500 times as a primary antibody and POD-labelled anti-mouse IgG as a secondary antibody. With respect to a negative serum, the ELISA method was carried out in the same manner as in Example 4. There was no difference in reactivity to the monoclonal antibody, and the FDX-fused proteins in both cases of HTLV-I and HTLV-II had lower reactivities to the negative serum. The results are shown in FIG. 6 and FIG. 7.

Reference Example 3

Preparation of Protein in Which GST and *Treponema pallidum* 15 Kda Antigen are Fused From syphilis bacteria (Nichols strain from *Treponema pallidum*) purified from pyphilis bacteria-subcultured rabbit testicles, genomic DNA was extracted. By using the extracted DNA as a template, a primer was produced based on the known DNA sequences by using a DNA synthesizer (Model 392, trade name, produced by PERKIN ELMER Co.). By using the primer, about 370 bp of a DNA fragment coding a surface antigen of 15 Kda (hereinafter referred to as "Tp15" in the specification) of *Treponema pallidum* (hereinafter referred to as "Tp", in the specification) was amplified with a thermal cycler (Model PJ1000, trade name, produced by PERKIN ELMER Co.). This DNA fragment was integrated into an EcoRI site of a GST-expressing type vector pWG6A in which DNA sequence of GST had been inserted into pW6A to obtain a vector pWGTp15 expressing a protein in which GST and Tp15 were fused (hereinafter referred to as "GST-15" in the specification). DNA sequence of the GST-15 inserted into the vector is shown in SEQ ID NO: 14 and amino acids sequence coded by said DNA sequence is shown in SEQ ID NO: 15. In the same manner as in Example 1, the vector was introduced into *Escherichia coli,* and expression of GST-15 was induced. A sample for electrophoresis was prepared under the same conditions as in Example 1. After subjecting to 12.5% SDS-PAGE according to the Laemmli method, one sheet of gel was subjected to CBB staining, and the other sheet was transferred to a nitrocellulose membrane by the method shown in Example 3. By using an anti-Tp15 monoclonal antibody as a primary antibody and a POD-labeled mouse IgG as a secondary antibody, these were reacted in the same method as in Example 3 and coloring was carried out by using 4-chloro-1-naphthol and hydrogen peroxide, a band was given at about 42 Kda which was the same position as that of the CBB-stained gel.

Reference Example 4

Preparation of Protein in Which TRX and Tp15 are Fused

A DNA fragment of Tp15 amplified in Reference example 3 was integrated into an EcoRI site of the TRX-expressing type vector pWT8A in which DNA sequence of TRX had been inserted into pW6A to obtain a vector pWTTp15 expressing a protein in which TRX and Tp15 were fused (hereinafter referred to as "TRX-15" in the specification). DNA sequence of the TRX-15 inserted into the vector is shown in SEQ ID NO: 16 and amino acids sequence coded by said DNA sequence is shown in SEQ ID NO: 17. In the same manner as in Example 1, the vector was introduced into *Escherichia coli,* and expression of TRX-15 was induced. A sample for electrophoresis was prepared under the same conditions as in Example 1. After subjecting to 12.5% SDS-PAGE according to the Laemmli method, one sheet of gel was subjected to CBB staining, and the other sheet was transferred to a nitrocellulose membrane by the method shown in Example 3. By using an anti-Tp15 monoclonal antibody as a primary antibody and a POD-labeled mouse IgG as a secondary antibody, these were reacted in the same method as in Example 3 and coloring was carried out by using 4-chloro-1-naphthol and hydrogen peroxide, a band was given at about 27 Kda which was the same position as that of the CBB-stained gel.

Example 9

Preparation of Protein in Which FDX and Tp15 are Fused

A DNA fragment of Tp15 amplified in Reference example 3 was integrated into an EcoRI, BamHI site of the FDX-expressing type vector pWF6A prepared in Example 1 to obtain a vector pWFTp15 expressing a protein in which FDX and Tp15 were fused (hereinafter referred to as "FDX-15" in the specification). DNA sequence of the FDX-15 inserted into the vector is shown in SEQ ID NO: 18 and amino acids sequence coded by said DNA sequence is shown in SEQ ID NO: 19. In the same manner as in Example 1, the vector was introduced into *Escherichia coli,* and expression of FDX-15 was induced. A sample for electrophoresis was prepared under the same conditions as in Example 1. After subjecting to 12.5% SDS-PAGE according to the Laemmli method, one sheet of gel was subjected to CBB staining, and the other sheet was transferred to a nitrocellulose membrane by the method shown in Example 3. By using an anti-Tp15 monoclonal antibody as a primary antibody and a POD-labeled mouse IgG as a secondary antibody, these were reacted in the same method as in Example 3 and coloring was carried out by using 4-chloro-1-naphthol and hydrogen peroxide, a band was given at about 30 Kda which was the same position as that of the CBB-stained gel.

Example 10

Heat Resistance Test of FDX-15, GST-15 and TRX-15

Figure 8:
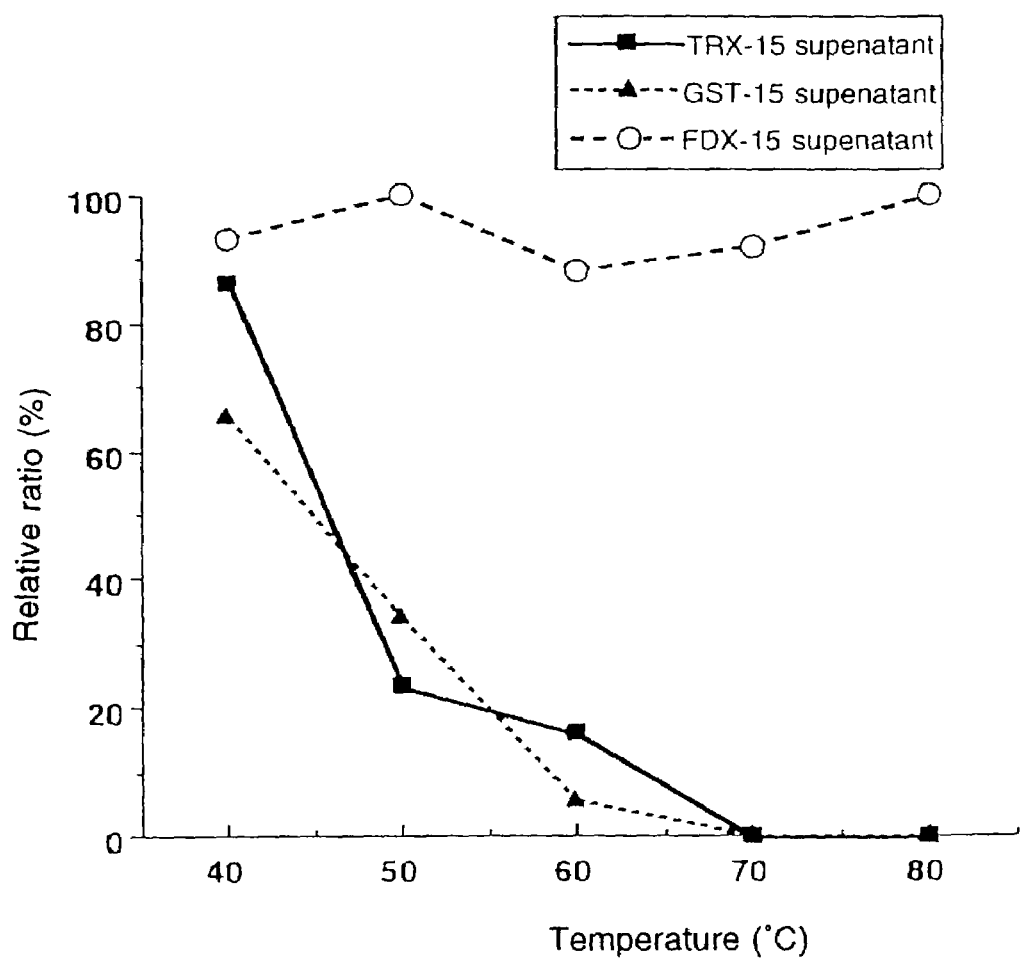
FIG. 8 is a graph showing the activity of a fused protein in a supernatant subjected to heat treatment.
Figure 9:
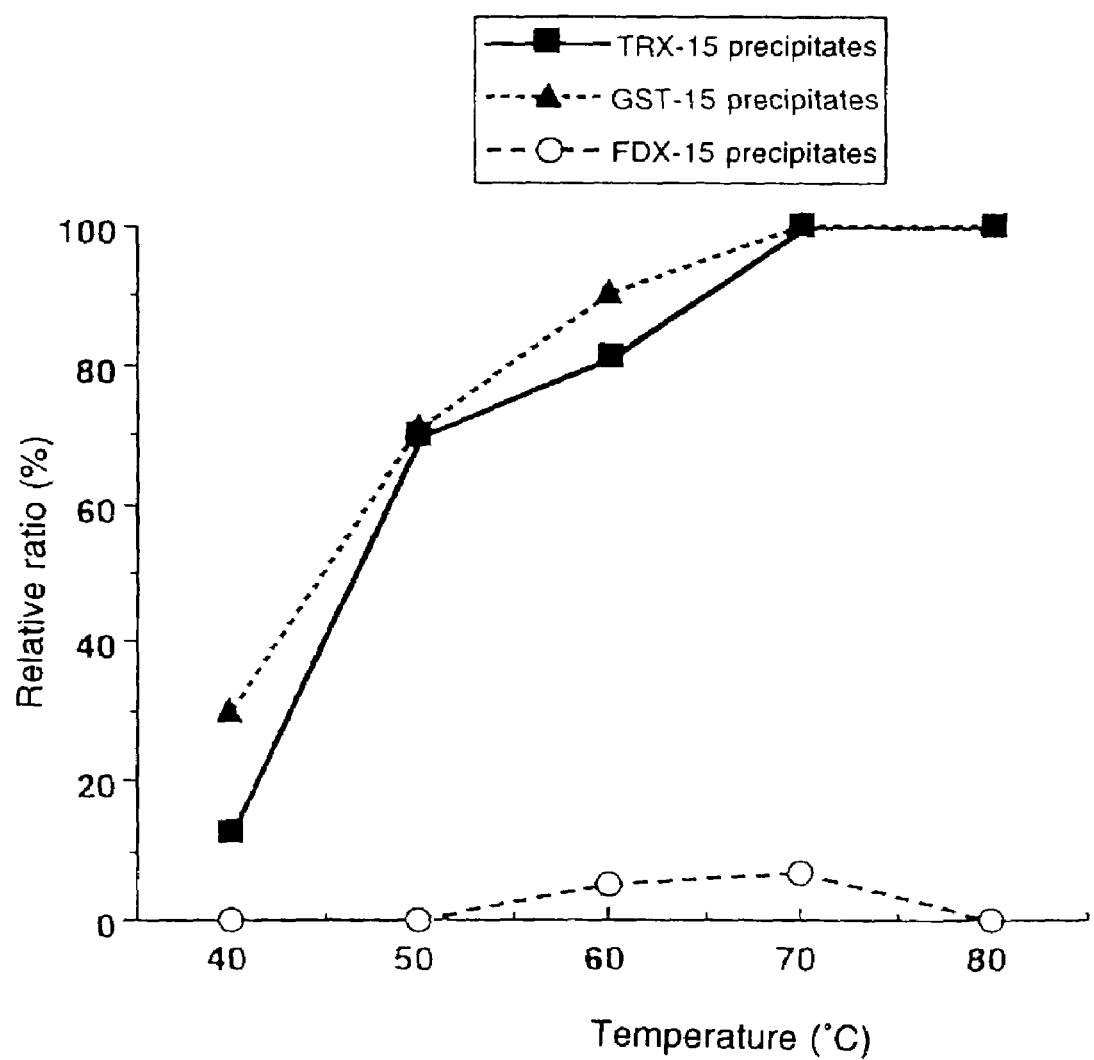
FIG. 9 is a graph showing the activity of a fused protein of precipitates subjected to heat treatment.

The vectors expressing FDX-15, GST-15 and TRX-15 prepared in Example 9, Reference example 3 and Reference example 4 were introduced into host *Escherichia coli* and then cultured under conditions of using 1 liter of the LB medium at 37° C., respectively. By preculture, a concentration of *Escherichia coli* in culture broths was made to have such turbidity that absorbance at a wavelength of 600 nm was about 1.0, 1 mM IPTG was added thereto to induce expression. After the cells were recovered by centrifugation, 200 ml of the Tris buffer was added to the cells. After sonication treatment under ice cooling, fused proteins were recovered in the centrifugation supernatants, respectively. 800 µl of these proteins were taken, respectively, and shaken for 13 minutes in water bath at 40° C., 50° C., 60° C., 70° C. and 80° C. The respective samples were centrifuged and then separated into supernatants and precipitates, and analysis was carried out by SDS-PAGE and the western blotting method. As a blocking agent of the western blotting method, 1% skim milk dissolved in PBS was used, and as a primary antibody, an anti-TP rabbit antibody was used. As a secondary antibody, a POD-labelled anti-rabbit antibody was used, and as a coloring agent, 4-chloro-1-naphthol and hydrogen peroxide were used. The result of coloring of western blotting was confirmed by a densitometer. The results are shown in FIG. 8 and FIG. 9. Precipitates of TRX-15 and GST-15 were partially generated at 40° C. by thermal denaturation, about 80% of TRX-15 and GST-15 were precipitated at 60° C., and about 100% of them were precipitated at 70° C. Almost no precipitate by thermal denaturation of FDX-15 was generated at 40° C. to 80° C., and even at 80° C., about 100% of FDX-15 existed in the supernatant.

Example 11

Purification of FDX-15 by Heat Treatment pWFTp15 prepared in Example 9 was introduced into host *Escherichia coli* and then cultured under conditions of using 1 liter of the LB medium at 37° C. By preculture, a concentration of *Escherichia coli* in culture broths was made to have such turbidity that absorbance at a wavelength of 600 nm was about 1.0, 1 mM IPTG was added thereto to induce expression. The cells were recovered by centrifugation. 200 ml of the Tris buffer was added to the cells, and the cells were sonicated to recover FDX-15 in the centrifugation supernatant. Then, by using a hot plate and a water bath, heat treatment at 70° C. for 10 minutes was carried out to recover FDX-15 in the centrifugation supernatant. The supernatant subjected to heat treatment was purified by a QFF anion exchange column (trade name, manufactured by Pharmacia Biotec Co.) equilibrated with the Tris buffer. When the supernatant was eluted by a column equilibrated buffer containing sodium chloride, FDX-15 was recovered at a concentration of about 0.3 M to 0.4 M sodium chloride-eluted fraction. Then, 10 mM DTT was added to the QFF recovered fraction, and the mixture was purified by using a RESOURCE RPC column (trade name, manufactured by Pharmacia Biotec Co.) equilibrated with a 20 mM sodium hydroxide solution. When the mixture was eluted by acetonitrile, FDX-15 was recovered at a concentration of about 20% to 25% acetonitrile-eluted fraction. This reverse phase recovered fraction was concentrated by Centriprep (trade name, manufactured by Amicon Inc.), and the concentrate was subjected to gel filtration by a Superdex 200 column (trade name, manufactured by Pharmacia Biotec Co.). When the filtrate was eluted by a buffer containing 6 M urea, 0.5 M sodium chloride and 20 mM Tris-hydrochloride having pH 8.0, purified FDX-15 was recovered at a molecular weight of about 50,000. By heat treatment at 60° C., about 80% of the *Escherichia coli* protein was precipitated by thermal denaturation, but even at 70° C., almost 100% of FDX-15 was recovered in the supernatant, and the purification degree was raised by about 5 times only by heat treatment.

Figure 10:
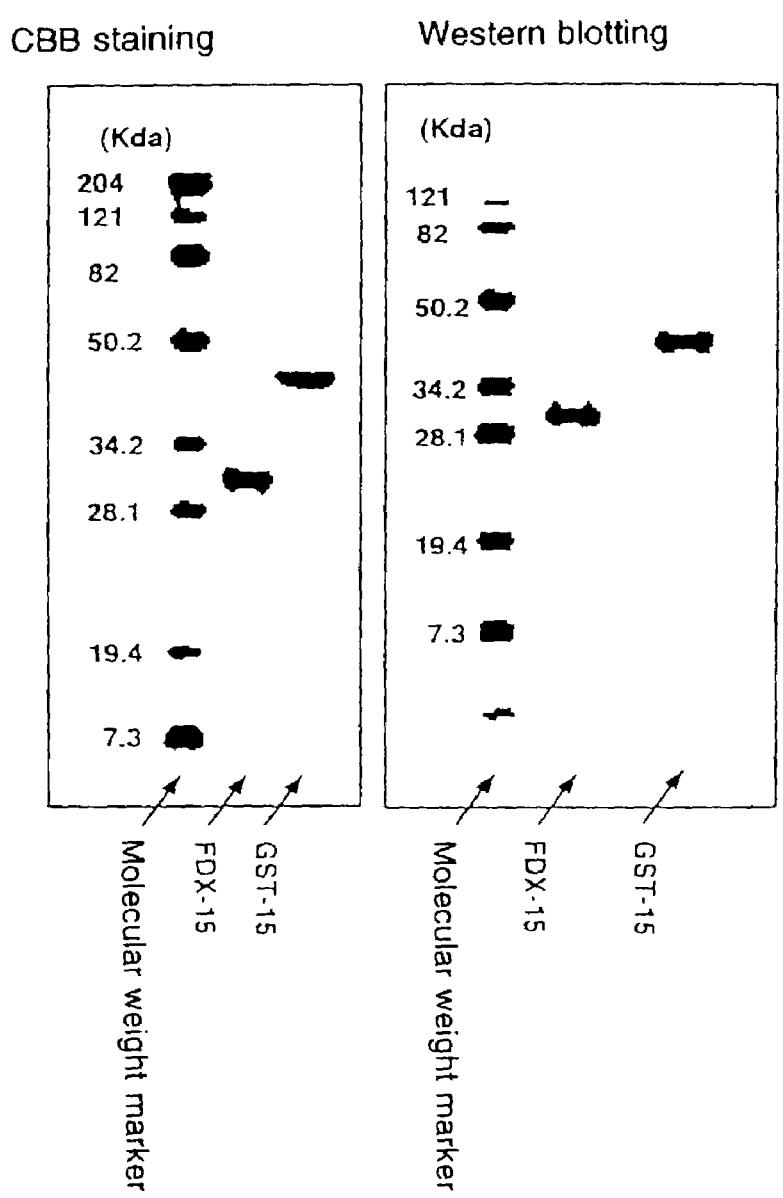
FIG. 10 is a view showing the activity of a fused protein after heat treatment and purification.

Further, GST-15 obtained by introducing pWGTp15 prepared in Reference example 3 into host *Escherichia coli*, carrying out induction and expression operations in the same manner therein and carrying out purification by a common column operation without carrying out heat treatment and FDX-15 purified by heat treatment were subjected to the western blotting method in the same manner as in Example 10 by using an anti-Tp rabbit antibody. It was shown that even though purification by heat treatment was carried out, FDX-15 retained reactivity. The results are shown in FIG. 10.

Example 12

Preparation of AK-expressing Vector pW6AK

Figure 11:
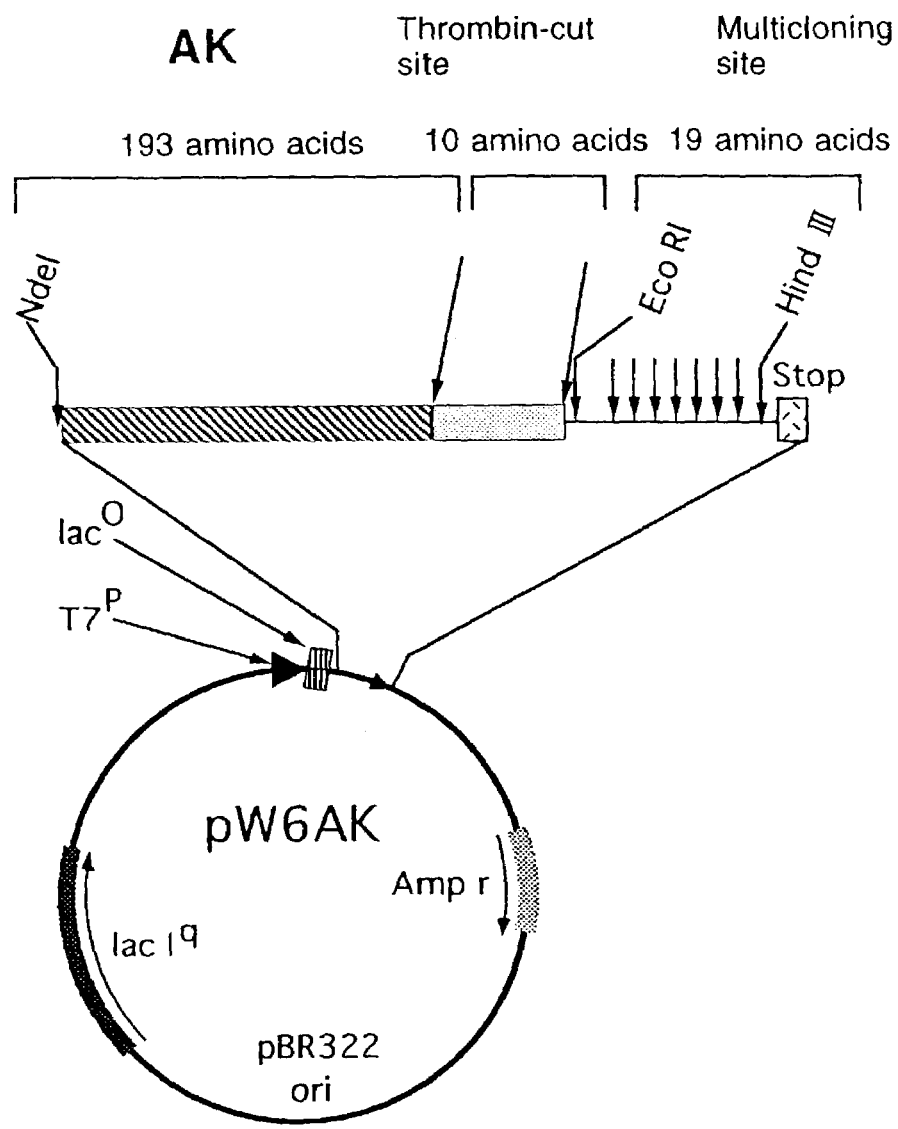
FIG. 11 is a detailed view of an expression vector pW6AK.

By using 16 primers of 53 mer prepared based on a known DNA sequence of AK derived from a *Sulfolobus bacterium* by using a DNA synthesizer (manufactured by Perkin Elmer Co.), genes of *Sulfolobus acidocaldarius* AK were synthesized by the assemble PCR method. In the assemble PCR method, a Taq polymerase (produced by Toyobo Co.) was used, and the total base number of 630 bp was amplified under conditions of 30 cycles of 94° C.-1 minute, 55° C.-1 minute and 72° C.-1 minute. A NdeI site was added to 5'-end, a restriction enzyme EcoRI was added to 3'-end, and a thrombin-cut site was added to C terminal. This fragment was integrated into the NdeI and EcoRI sites of 4.6 Kb of a pW6A vector prepared from pGEMEX-1 (trade name, produced by Promega Co.) and pGEX-2T (trade name, produced by Pharmacia Biotec Co.) to prepare pW6AK as a vector expressing AK. A detailed view of pW6AK is shown in FIG. 11. pW6AK contains genes of a fused protein comprising 223 amino acids including 194 amino acids derived from AK, 10 amino acids derived from a thrombin-cleaved site and 19 amino acids derived from multi cloning site of pW6A, at the NdeI and EcoRI sites. The base sequence of the inserted fragment was confirmed by a DNA sequence kit (trade name: Sequenase kit Ver. 2.0, produced by Amersham United States Biochemical Co.). DNA sequence of the AK inserted into the pW6A is shown in SEQ ID NO: 3 and amino acids sequence coded by said DNA sequence is shown in SEQ ID NO: 4. pW6AK was introduced into host *Escherichia coli* and then cultured for 2 hours in the LB medium. Thereafter, 1 mM IPTG was added thereto, and the mixture was cultured for 2 hours to induce expression. The TE buffer were added to the precipitates of *Escherichia coli*, the precipitates were sonicated, and 15% SDS-PAGE according to the Laemmli method was carried out. By CBB staining, a band was confirmed at about 40 Kda.

Example 13

Purification of AK pW6AK prepared in Example 12 was introduced into host *Escherichia coli* and then cultured under conditions of using the LB medium at 37° C. By preculture, a concentration of *Escherichia coli* in culture broth was made to have such turbidity that absorbance at a wavelength of 600 nm was about 1.0, 1 mM IPTG was added thereto to induce expression. After the mixture was cultured for 3 hours, centrifugation was carried out to recover *Escherichia coli*. 200 ml of the Tris buffer was added to recover *Escherichia coli*, followed by sonication treatment under ice cooling. After centrifugation, the expressed fused protein was recovered in the supernatant as a soluble component. When this supernatant was subjected to heat treatment at 65° C. for 10 minutes, about 70% of the *Escherichia coli* protein was thermally denatured and precipitated, and 80% or more of AK was recovered in the centrifugation supernatant after the heat treatment.

This supernatant was purified by a Hydroxy apatite column (manufactured by Bio-rad Lab.) equilibrated with the Tris buffer. When the supernatant was eluted by a sodium phosphate buffer, AK was recovered at a concentration of about 0.2 M sodium phosphate-eluted fraction. Then, this AK fraction was purified by gel filtration using a Superdex 200 26/60 column (trade name, manufactured by Pharmacia Biotec Co.) equilibrated with a buffer containing 6 M urea, 0.5 M sodium chloride and 20 mM Tris-hydrochloride having pH 9.4. At a fraction of a molecular weight being about 20,000, purified AK was recovered.

Example 14

Preparation of Protein in Which AK and Tp15 are Fused

A DNA fragment of Tp15 amplified in Reference example 3 was integrated into the AK-expressing type vector pW6AK prepared in Example 12 to obtain a vector pW6AKTp15 expressing a protein in which AK and Tp15 were fused (hereinafter referred to as "AK-15" in the specification). DNA sequence of the AK-15 inserted into the vector is shown in SEQ ID NO: 20 and amino acids sequence coded by said DNA sequence is shown in SEQ ID NO: 21. In the same manner as in Example 1, the vector was introduced into *Escherichia coli,* and expression of AK-15 was induced. A sample for electrophoresis was prepared under the same conditions as in Example 1. After subjecting to 12.5% SDS-PAGE according to the Laemmli method, one sheet of gel was subjected to CBB staining, and the other sheet was transferred to a nitrocellulose membrane by the method shown in Example 3. By using an anti-Tp15 monoclonal antibody as a primary antibody and a POD-labeled mouse IgG as a secondary antibody, these were reacted in the same method as in Example 3 and coloring was carried out by using 4-chloro-1-naphthol and hydrogen peroxide, a band was given at about 40 Kda which was the same position as that of the CBB-stained gel.

Example 15

Purification of AK-15 by Heat Treatment pWAKTp15 prepared in Example 14 was introduced into host *Escherichia coli* and then cultured under conditions of using 1 liter of the LB medium at 37° C. By preculture, a concentration of *Escherichia coli* in culture broth was made to have such turbidity that absorbance at a wavelength of 600 nm was about 1.0, 1 mM IPTG was added thereto to induce expression. The cells were recovered by centrifugation. 200 ml of a 50 mM glycine-sodium hydroxide buffer having pH 10.0 was added to the cells, and the cells were sonicated to recover AK-15 in the centrifugation supernatant. Then, by using a hot plate, heat treatment at 60° C. for 10 minutes was carried out to recover AK-15 in the centrifugation supernatant. The supernatant subjected to heat treatment was dialyzed to a 4 M urea-50 mM sodium acetate buffer having pH 6.0 and then purified by a SFF cation exchange column (trade name, manufactured by Pharmacia Biotec Co.) equilibrated with said buffer. When the supernatant was eluted by a column equilibrated buffer containing sodium chloride, AK-15 was recovered at a concentration of about 0.2 M to 0.4 M sodium chloride-eluted fraction. The recovered AK-15 fraction was purified by gel filtration using a Superdex 200 26/60 column (trade name, manufactured by Pharmacia Biotec Co.) equilibrated with a buffer containing 6 M urea, 0.5 M sodium chloride and 20 mM Tris-hydrochloride having pH 9.4. At a fraction of a molecular weight being about 40,000, purified AK-15 was recovered.

Figure 12:
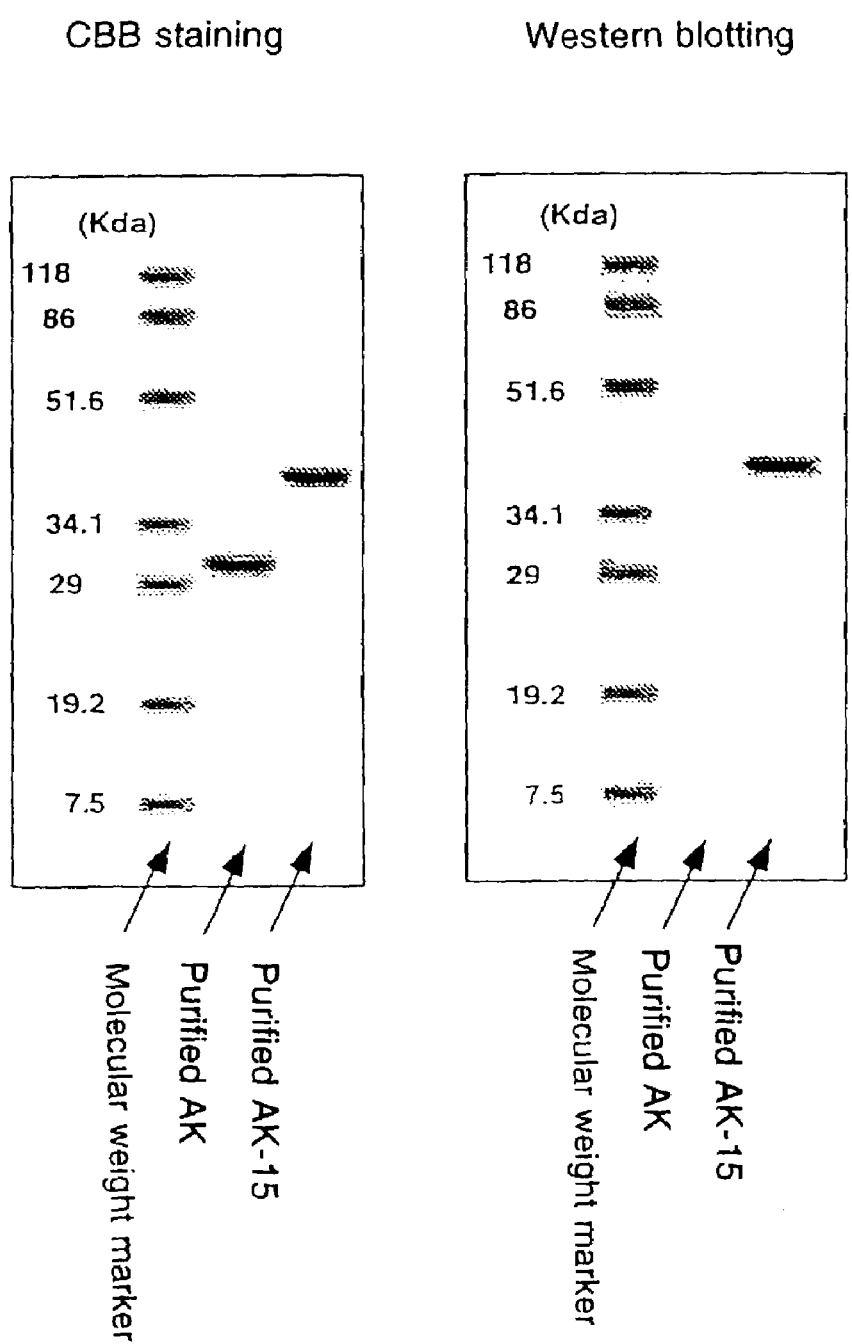
FIG. 12 is a view showing the activity of a fused protein after heat treatment and purification.

When the western blotting method was carried out in the same manner as in Example 1 by using an anti-Tp rabbit antibody, it was shown that even though purification by heat treatment was carried out, AK-15 retained reactivity. The results are shown in FIG. 12.

According to the present invention, a fused DNA sequence having more excellent operatability and productivity than those of a conventional DNA sequence coding a fused protein, a fused protein expressed from said fused DNA sequence, and a method for expressing the fused protein by using said DNA sequence.

The invention claimed is:

1. A fused protein expressed from a fused DNA sequence which comprises a first DNA sequence encoding a heat-resistant ferredoxin or a heat-resistant adenylate kinase fused directly or indirectly to the 5' end of a second DNA sequence encoding a selected protein or peptide in a reading frame, so that
   (1) the fused DNA sequence produces a protein in which the heat-resistant ferredoxin or the heat-resistant adenylate kinase is attached to the amino terminus of the selected protein or peptide when expressed in a host cell, and
   (2) the fused DNA is expressed in the host cell at a higher level as compared to a corresponding DNA which comprises the DNA sequence encoding a selected protein or peptide but does not comprise the DNA sequence encoding a heat-resistant ferredoxin or a heat-resistant adenylate kinase.

2. The fused protein according to claim 1, wherein the first DNA sequence encodes a heat-resistant ferredoxin.

3. The fused protein according to claim 1, wherein the first DNA sequence encodes a heat-resistant adenylate kinase.

4. The fused protein according to claim 1, wherein the first DNA sequence encodes a heat-resistant ferredoxin from a *Pyrococcus bacterium*.

5. A fused protein according to claim 1, wherein the first DNA sequence encodes a heat-resistant adenylate kinase from a *Sulfolobus bacterium*.

* * * * *

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 291 base pairs
      (B) TYPE: nucleic acid
      (C) STRANDEDNESS: double
      (D) TOPOLOGY: linear (ii) MOLECULE TYPE: other nucleic acid (vi) ORIGINAL SOURCE:
      (A) ORGANISM: SYNTHESIZED (x) PUBLICATION INFORMATION:
      (A) AUTHORS: NOBUYUKI FUJII ET AL,
      (B) TITLE: FUSED DNA SEQUENCE, FUSED PROTEIN EXPRESSED
          FROM SAID FUSED DNA SEQUENCE AND METHOD FOR
          EXPRESSING SAID FUSED PROTEIN
      (K) RELEVANT RESIDUES IN SEQ ID NO:1: FROM 1 TO 291

(xi) SEQUENCE DESCRIPTION: SEQ ID NO: 1:

```
ATGGCGTGGA AGGTTTCTGT CGACCAAGAC ACCTGTATAG GAGATGCCAT CTGTGCAAGC        60

CTCTGTCCAG ACGTCTTTGA GATGAACGAT GAAGGAAAGG CCCAACCAAA GGTAGAGGTT       120
```

| | |
|---|---|
| ATTGAGGACG AAGAGCTCTA CAACTGTGCT AAGGAAGCTA TGGAGGCCTG TCCAGTTAGT | 180 |
| GCTATTACTA TTGAGGAGGC TGGTGGTTCT TCTCTGGTTC CGCGTGGATC GGAATTCGTC | 240 |
| GACCTCGAGG GATCCGGGCC CTCTAGATGC GGCCGCATGC ATGGTACCTA A | 291 |

(2) INFORMATION FOR SEQ ID NO: 2:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:2: FROM 1 TO 96

(xi) SEQUENCE DESCRIPTION: SEQ ID NO: 2:

```
Met Ala Trp Lys Val Ser Val Asp Gln Asp Thr Cys Ile Gly Asp Ala
 1               5                  10                  15

Ile Cys Ala Ser Leu Cys Pro Asp Val Phe Glu Met Asn Asp Glu Gly
                20                  25                  30

Lys Ala Gln Pro Lys Val Glu Val Ile Glu Asp Glu Glu Leu Tyr Asn
            35                  40                  45

Cys Ala Lys Glu Ala Met Glu Ala Cys Pro Val Ser Ala Ile Thr Ile
50                  55                  60

Glu Glu Ala Gly Gly Ser Ser Leu Val Pro Arg Gly Ser Glu Phe Val
65                  70                  75                  80

Asp Leu Glu Gly Ser Gly Pro Ser Arg Cys Gly Arg Met His Gly Thr
                85                  90                  95
```

(2) INFORMATION FOR SEQ ID NO: 3:

(i) SEQUENCE CHARACTERISTICS:
        (A) LENGTH: 672 base pairs
        (B) TYPE: nucleic acid
        (C) STRANDEDNESS: double
        (D) TOPOLOGY: linear (ii) MOLECULE TYPE: other nucleic acid (vi) ORIGINAL SOURCE:
        (A) ORGANISM: SYNTHESIZED (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:3: FROM 1 TO 672

(xi) SEQUENCE DESCRIPTION: SEQ ID NO: 3:

| | |
|---|---|
| ATGAAGATTG GTATTGTAAC TGGTATCCCT GGTGTAGGGA AAAGTACTGT CTTGGCTAAA | 60 |
| GTTAAAGAGA TATTGGATAA TCAAGGTATA AATAACAAGA TCATAAATTA TGGAGATTTT | 120 |
| ATGTTAGCAA CAGCATTAAA ATTAGGCTAT GCTAAAGATA GAGACGAAAT GAGAAAATTA | 180 |
| TCTGTAGAAA AGCAGAAGAA ATTGCAGATT GATGCGGCTA AAGGTATAGC TGAAGAGGCA | 240 |
| AGAGCAGGTG GAGAAGGATA TCTGTTCATA GATACGCACG CTGTGATACG TACACCCTCT | 300 |

-continued

```
GGATATTTAC CTGGTTTACC GTCAGATATA ATTACAGAAA TAAATCCGTC TGTTATCTTT     360

TTACTGGAAG CTGATCCTAA GATAATATTA TCAAGGCAAA AGAGAGATAC AACAAGGAAT     420

AGAAATGATT ATAGTGACGA ATCAGTTATA TTAGAAACCA TAAACTTCGC TAGATATGCA     480

GCTACTGCTT CTGCAGTATT AGCCGGTTCT ACTGTTAAGG TAATTGTAAA CGTGGAAGGA     540

GATCCTAGTA TAGCAGCTAA TGAGATAATA AGGTCTATGA AGGGTGGTTC TTCTCTGGTT     600

CCGCGTGGAC TGGAATTCGT CGACCTCGAG GGATCCGGGC CCTCTAGATG CGGCCGCATG     660

CATGGTACCT AA                                                        672
```

(2) INFORMATION FOR SEQ ID NO: 4:

(i) SEQUENCE CHARACTERISTICS:
        (A) LENGTH: 223 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:4: FROM 1 TO 223

(xi) SEQUENCE DESCRIPTION: SEQ ID NO: 4:

```
Met Lys Ile Gly Ile Val Thr Gly Ile Pro Gly Val Gly Lys Ser Thr
1               5                  10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
        35                  40                  45

Gly Tyr Ala Lys Asp Arg Asp Glu Met Arg Lys Leu Ser Val Glu Lys
    50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Asp Ile Ile Thr
            100                 105                 110

Glu Ile Asn Pro Ser Val Ile Phe Leu Leu Glu Ala Asp Pro Lys Ile
        115                 120                 125

Ile Leu Ser Arg Gln Lys Arg Asp Thr Thr Arg Asn Arg Asn Asp Tyr
    130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
            180                 185                 190

Met Lys Gly Gly Ser Ser Leu Val Pro Arg Gly Leu Glu Phe Val Asp
        195                 200                 205

Leu Glu Gly Ser Gly Pro Ser Arg Cys Gly Arg Met His Gly Thr
    210                 215                 220
```

(2) INFORMATION FOR SEQ ID NO: 5:

(i) SEQUENCE CHARACTERISTICS:
        (A) LENGTH: 4557 base pairs
        (B) TYPE: nucleic acid
        (C) STRANDEDNESS: double
        (D) TOPOLOGY: circular (ii) MOLECULE TYPE: other nucleic acid (vi) ORIGINAL SOURCE:
        (A) ORGANISM: E. COLI
        (B) STRAIN: BL21 (DE3)

(x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:5: FROM 1 TO 4557

(xi) SEQUENCE DESCRIPTION: SEQ ID NO: 5:

```
ATGGCTAGCG AATTCGTCGA CCTCGAGGGA TCCGGGCCCT CTAGATGCGG CCGCATGCAT      60
GGTACCTAAC TAACTAAGCT TGAGTATTCT ATAGTGTCAC CTAAATCCCA GCTTGATCCG     120
GCTGCTAACA AAGCCCGAAA GGAAGCTGAG TTGGCTGCTG CCACCGCTGA GCAATAACTA     180
GCATAACCCC TTGGGGCCTC TAAACGGGTC TTGAGGGGTT TTTTGCTGAA AGGAGGAACT     240
ATATCCGGAT AACCTGGCGT AATAGCGAAG AGGCCCGCAC CGAATTAATT CATCGTGACT     300
GACTGACGAT CTGCCTCGCG CGTTTCGGTG ATGACGGTGA AAACCTCTGA CACATGCAGC     360
TCCCGGAGAC GGTCACAGCT TGTCTGTAAG CGGATGCCGG GAGCAGACAA GCCCGTCAGG     420
GCGCGTCAGC GGGTGTTGGC GGGTGTCGGG GCGCAGCCAT GACCCAGTCA CGTAGCGATA     480
GCGGAGTGTA TAATTCTTGA AGACGAAAGG GCCTCGTGAT ACGCCTATTT TTATAGGTTA     540
ATGTCATGAT AATAATGGTT TCTTAGACGT CAGGTGGCAC TTTTCGGGGA AATGTGCGCG     600
GAACCCCTAT TTGTTTATTT TTCTAAATAC ATTCAAATAT GTATCCGCTC ATGAGACAAT     660
AACCCTGATA AATGCTTCAA TAATATTGAA AAAGGAAGAG TATGAGTATT CAACATTTCC     720
GTGTCGCCCT TATTCCCTTT TTTGCGGCAT TTTGCCTTCC TGTTTTTGCT CACCCAGAAA     780
CGCTGGTGAA AGTAAAAGAT GCTGAAGATC AGTTGGGTGC ACGAGTGGGT TACATCGAAC     840
TGGATCTCAA CAGCGGTAAG ATCCTTGAGA GTTTTCGCCC CGAAGAACGT TTTCCAATGA     900
TGAGCACTTT TAAAGTTCTG CTATGTGGCG CGGTATTATC CCGTGTTGAC GCCGGGCAAG     960
AGCAACTCGG TCGCCGCATA CACTATTCTC AGAATGACTT GGTTGAGTAC TCACCAGTCA    1020
CAGAAAAGCA TCTTACGGAT GGCATGACAG TAAGAGAATT ATGCAGTGCT GCCATAACCA    1080
TGAGTGATAA CACTGCGGCC AACTTACTTC TGACAACGAT CGGAGGACCG AAGGAGCTAA    1140
CCGCTTTTTT GCACAACATG GGGGATCATG TAACTCGCCT TGATCGTTGG GAACCGGAGC    1200
TGAATGAAGC CATACCAAAC GACGAGCGTG ACACCACGAT GCCTGCAGCA ATGGCAACAA    1260
CGTTGCGCAA ACTATTAACT GGCGAACTAC TTACTCTAGC TTCCCGGCAA CAATTAATAG    1320
ACTGGATGGA GGCGGATAAA GTTGCAGGAC CACTTCTGCG CTCGGCCCTT CCGGCTGGCT    1380
GGTTTATTGC TGATAAATCT GGAGCCGGTG AGCGTGGGTC TCGCGGTATC ATTGCAGCAC    1440
TGGGGCCAGA TGGTAAGCCC TCCCGTATCG TAGTTATCTA CACGACGGGG AGTCAGGCAA    1500
CTATGGATGA ACGAAATAGA CAGATCGCTG AGATAGGTGC CTCACTGATT AAGCATTGGT    1560
AACTGTCAGA CCAAGTTTAC TCATATATAC TTTAGATTGA TTTAAAACTT CATTTTTAAT    1620
```

```
TTAAAAGGAT CTAGGTGAAG ATCCTTTTTG ATAATCTCAT GACCAAAATC CCTTAACGTG   1680

AGTTTTCGTT CCACTGAGCG TCAGACCCCG TAGAAAAGAT CAAAGGATCT TCTTGAGATC   1740

CTTTTTTTCT GCGCGTAATC TGCTGCTTGC AAACAAAAAA ACCACCGCTA CCAGCGGTGG   1800

TTTGTTTGCC GGATCAAGAG CTACCAACTC TTTTTCCGAA GGTAACTGGC TTCAGCAGAG   1860

CGCAGATACC AAATACTGTC CTTCTAGTGT AGCCGTAGTT AGGCCACCAC TTCAAGAACT   1920

CTGTAGCACC GCCTACATAC CTCGCTCTGC TAATCCTGTT ACCAGTGGCT GCTGCCAGTG   1980

GCGATAAGTC GTGTCTTACC GGGTTGGACT CAAGACGATA GTTACCGGAT AAGGCGCAGC   2040

GGTCGGGCTG AACGGGGGGT TCGTGCACAC AGCCCAGCTT GGAGCGAACG ACCTACACCG   2100

AACTGAGATA CCTACAGCGT GAGCTATGAG AAAGCGCCAC GCTTCCCGAA GGGAGAAAGG   2160

CGGACAGGTA TCCGGTAAGC GGCAGGGTCG GAACAGGAGA GCGCACGAGG GAGCTTCCAG   2220

GGGGAAACGC CTGGTATCTT TATAGTCCTG TCGGGTTTCG CCACCTCTGA CTTGAGCGTC   2280

GATTTTTGTG ATGCTCGTCA GGGGGGCGGA GCCTATGGAA AAACGCCAGC AACGCGGCCT   2340

TTTTACGGTT CCTGGCCTTT TGCTGGCCTT TTGCTCACAT GTTCTTTCCT GCGTTATCCC   2400

CTGATTCTGT GGATAACCGT ATTACCGCCT TTGAGTGAGC TGATACCGCT CGCCGCAGCC   2460

GAACGACCGA GCGCAGCGAG TCAGTGAGCG AGGAAGCGGA AGAGCGCCTG ATGCGGTATT   2520

TTCTCCTTAC GCATCTGTGC GGTATTTCAC ACCGCATAAA TTCCGACACC ATCGAATGGT   2580

GCAAAACCTT TCGCGGTATG GCATGATAGC GCCCGGAAGA GAGTCAATTC AGGGTGGTGA   2640

ATGTGAAACC AGTAACGTTA TACGATGTCG CAGAGTATGC CGGTGTCTCT TATCAGACCG   2700

TTTCCCGCGT GGTGAACCAG GCCAGCCACG TTTCTGCGAA AACGCGGGAA AAAGTGGAAG   2760

CGGCGATGGC GGAGCTGAAT TACATTCCCA ACCGCGTGGC ACAACAACTG GCGGGCAAAC   2820

AGTCGTTGCT GATTGGCGTT GCCACCTCCA GTCTGGCCCT GCACGCGCCG TCGCAAATTG   2880

TCGCGGCGAT TAAATCTCGC GCCGATCAAC TGGGTGCCAG CGTGGTGGTG TCGATGGTAG   2940

AACGAAGCGG CGTCGAAGCC TGTAAAGCGG CGGTGCACAA TCTTCTCGCG CAACGCGTCA   3000

GTGGGCTGAT CATTAACTAT CCGCTGGATG ACCAGGATGC CATTGCTGTG GAAGCTGCCT   3060

GCACTAATGT TCCGGCGTTA TTTCTTGATG TCTCTGACCA GACACCCATC AACAGTATTA   3120

TTTTCTCCCA TGAAGACGGT ACGCGACTGG GCGTGGAGCA TCTGGTCGCA TTGGGTCACC   3180

AGCAAATCGC GCTGTTAGCG GGCCCATTAA GTTCTGTCTC GGCGCGTCTG CGTCTGGCTG   3240

GCTGGCATAA ATATCTCACT CGCAATCAAA TTCAGCCGAT AGCGGAACGG GAAGGCGACT   3300

GGAGTGCCAT GTCCGGTTTT CAACAAACCA TGCAAATGCT GAATGAGGGC ATCGTTCCCA   3360

CTGCGATGCT GGTTGCCAAC GATCAGATGG CGCTGGGCGC AATGCGCGCC ATTACCGAGT   3420

CCGGGCTGCG CGTTGGTGCG GATATCTCGG TAGTGGGATA CGACGATACC GAAGACAGCT   3480

CATGTTATAT CCCGCCGTTA ACCACCATCA AACAGGATTT TCGCCTGCTG GGGCAAACCA   3540

GCGTGGACCG CTTGCTGCAA CTCTCTCAGG GCCAGGCGGT GAAGGGCAAT CAGCTGTTGC   3600

CCGTCTCACT GGTGAAAAGA AAAACCACCC TGGCGCCCAA TACGCAAACC GCCTCTCCCC   3660

GCGCGTTGGC CGATTCATTA ATGCAGCTGG CACGACAGGT TTCCCGACTG GAAAGCGGGC   3720

AGTGAGCGCA ACGCAATTAA TGTGAGTTAG CTCACTCATT AGGCACCCCA GGCTTTACAC   3780

TTTATGCTTC CGGCTCGTAT GTTGTGTGGA ATTGTGAGCG GATAACAATT TCACACAGGA   3840

AACAGCTATG ACCATGATTA CGGATTCACT GGCCGTCGTT TTACAACGTC GTGACTGGGA   3900

AAACCCTGGC GTTACCCAAC TTAATCGCCT TGCAGCACAT CCCCCTTTCG CCAGCTGGCG   3960

TAATAGCGAA GAGGCCCGCA CCGATCGCCC TTCCCAACAG TTGCGCAGCC TGAATGGCGA   4020
```

```
ATGGCGCTTT GCCTGGTTTC CGGCACCAGA AGCGGTGCCG GAAAGCTGGC TGGAGTGCGA    4080

TCTTCCTGAG GCCGATACTG TCGTCGTCCC CTCAAACTGG CAGATGCACG GTTACGATGC    4140

GCCCATCTAC ACCAACGTAA CCTATCCCAT TACGGTCAAT CCGCCGTTTG TTCCCACGGA    4200

GAATCCGACG GGTTGTTACT CGCTCACATT TAATGTTGAT GAAAGCTGGC TACAGGAAGG    4260

CCAGACGCGA ATTATTTTTG ATGGCGTTGG AATTACGTTA TCGACTGCAC GGTGCACCAA    4320

TGCTTCTGGC GTCAGGCAGC CATCGGAAGC TGTGGTATGG CTGTGCAGGT CGTAAATCAC    4380

TGCATAATTC GTGTCGCTCA AGGCGCACTC CCGTTCTGGA TAATGTTTTT TGCGCCGACA    4440

TCATAACGGT TCTGGCAAAT GGGAATTGGG AAATTAATAC GACTCACTAT ATGGAATTGT    4500

GAGCGGATAA CAATTCCTAG AAATAATTTT GTTTAACTTT AAGAAGGAGA TATACAT      4557
```

(2) INFORMATION FOR SEQ ID NO: 6:

(i) SEQUENCE CHARACTERISTICS:
        (A) LENGTH: 672 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: SYNTHESIZED, HTLV-1

(x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:6: FROM 1 TO 672

(xi) SEQUENCE DESCRIPTION: SEQ ID NO: 6:

```
ATGGCGTGGA AGGTTTCTGT CGACCAAGAC ACCTGTATAG GAGATGCCAT CTGTGCAAGC     60

CTCTGTCCAG ACGTCTTTGA GATGAACGAT GAAGGAAAGG CCCAACCAAA GGTAGAGGTT    120

ATTGAGGACG AAGAGCTCTA CAACTGTGCT AAGGAAGCTA TGGAGGCCTG TCCAGTTAGT    180

GCTATTACTA TTGAGGAGGC TGGTGGTTCT TCTCTGGTTC CGCGTGGATC GGAATTCATG    240

GGCCAAATCT TTTCCCGTAG CGCTAGCCCT ATTCCGCGGC CGCCCCGGGG GCTGGCCGCT    300

CATCACTGGC TTAACTTCCT CCAGGCGGCA TATCGCCTAG AACCCGGTCC CTCCAGTTAC    360

GATTTCCACC AGTTAAAAAA ATTTCTTAAA ATAGCTTTAG AAACACCGGT CTGGATCTGC    420

CCCATTAACT ACTCCCTCCT AGCCAGCCTA CTCCCAAAAG GATACCCCGG CCGGGTGAAT    480

GAAATTTTAC ACATACTCAT CCAAACCCAA GCCCAGATCC CGTCCCGCCC CGCGCCGCCG    540

CCGCCGTCAT CCTCCACCCA CGACCCCCCG GATTCTGACC CACAAATCCC CCCTCCCTAT    600

GTTGAGCCTA CAGCCCCCCA AGTCCTTTAA GGATCCGGGC CCTCTAGATG CGGCCGCATG    660

CATGGTACCT AA                                                        672
```

(2) INFORMATION FOR SEQ ID NO: 7:

(i) SEQUENCE CHARACTERISTICS:
        (A) LENGTH: 209 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
    (A) AUTHORS: NOBUYUKI FUJII ET AL,
    (B) TITLE: FUSED DNA SEQUENCE, FUSED PROTEIN EXPRESSED
        FROM SAID FUSED DNA SEQUENCE AND METHOD OF
        EXPRESSING SAID FUSED PROTEIN
    (K) RELEVANT RESIDUES IN SEQ ID NO:7: FROM 1 TO 209

(xi) SEQUENCE DESCRIPTION: SEQ ID NO: 7:

```
Met Ala Trp Lys Val Ser Val Asp Gln Asp Thr Cys Ile Gly Asp Ala
1               5                   10                  15

Ile Cys Ala Ser Leu Cys Pro Asp Val Phe Glu Met Asn Asp Glu Gly
            20                  25                  30

Lys Ala Gln Pro Lys Val Glu Val Ile Glu Asp Glu Glu Leu Tyr Asn
        35                  40                  45

Cys Ala Lys Glu Ala Met Glu Ala Cys Pro Val Ser Ala Ile Thr Ile
    50                  55                  60

Glu Glu Ala Gly Gly Ser Ser Leu Val Pro Arg Gly Ser Glu Phe Met
65                  70                  75                  80

Gly Gln Ile Phe Ser Arg Ser Ala Ser Pro Ile Pro Arg Pro Pro Arg
                85                  90                  95

Gly Leu Ala Ala His His Trp Leu Asn Phe Leu Gln Ala Ala Tyr Arg
            100                 105                 110

Leu Glu Pro Gly Pro Ser Ser Tyr Asp Phe His Gln Leu Lys Lys Phe
        115                 120                 125

Leu Lys Ile Ala Leu Glu Thr Pro Val Trp Ile Cys Pro Ile Asn Tyr
    130                 135                 140

Ser Leu Leu Ala Ser Leu Leu Pro Lys Gly Tyr Pro Gly Arg Val Asn
145                 150                 155                 160

Glu Ile Leu His Ile Leu Ile Gln Thr Gln Ala Gln Ile Pro Ser Arg
                165                 170                 175

Pro Ala Pro Pro Pro Ser Ser Ser Thr His Asp Pro Pro Asp Ser
            180                 185                 190

Asp Pro Gln Ile Pro Pro Pro Tyr Val Glu Pro Thr Ala Pro Gln Val
        195                 200                 205

Leu
```

(2) INFORMATION FOR SEQ ID NO: 8:

(i) SEQUENCE CHARACTERISTICS:
        (A) LENGTH: 690 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: SYNTHESIZED, HTLV-II (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:8: FROM 1 TO 690

(xi) SEQUENCE DESCRIPTION: SEQ ID NO: 8:

```
ATGGCGTGGA AGGTTTCTGT CGACCAAGAC ACCTGTATAG GAGATGCCAT CTGTGCAAGC      60

CTCTGTCCAG ACGTCTTTGA GATGAACGAT GAAGGAAAGG CCCAACCAAA GGTAGAGGTT     120

ATTGAGGACG AAGAGCTCTA CAACTGTGCT AAGGAAGCTA TGGAGGCCTG TCCAGTTAGT     180
```

-continued

```
GCTATTACTA TTGAGGAGGC TGGTGGTTCT TCTCTGGTTC CGCGTGGATC GGAATTCATG    240

GGACAAATCC ACGGGCTTTC CCCAACTCCA ATACCCAAAG CCCCCAGGGG GCTATCAACC    300

CACCACTGGC TTAACTTTCT CCAGGCTGCT TACCGCTTGC AGCCTAGGCC CTCCGATTTC    360

GACTTCCAGC AGCTACGACG CTTTCTAAAA CTAGCCCTTA AAACGCCCAT TTGGCTAAAT    420

CCTATTGACT ACTCGCTTTT AGCTAGCCTT ATCCCCAAGG GATATCCAGG AAGGGTGGTA    480

GAGATTATAA ATATCCTTGT CAAAAATCAA GTCTCCCCTA GCGCCCCCGC CGCCCCAGTT    540

CCGACACCTA TCTGCCCTAC TACTACTCCT CCGCCACCTC CCCCCCCTTC CCCGGAGGCC    600

CATGTTCCCC CCCCTTACGT GGAACCCACC ACCACGCAAT GCTTCTAAGG ATCCGGGCCC    660

TCTAGATGCG GCCGCATGCA TGGTACCTAA                                    690
```

(2) INFORMATION FOR SEQ ID NO: 9:

(i) SEQUENCE CHARACTERISTICS:
        (A) LENGTH: 215 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:9: FROM 1 TO 215

(xi) SEQUENCE DESCRIPTION: SEQ ID NO: 9:

```
Met Ala Trp Lys Val Ser Val Asp Gln Asp Thr Cys Ile Gly Asp Ala
1               5                   10                  15

Ile Cys Ala Ser Leu Cys Pro Asp Val Phe Glu Met Asn Asp Glu Gly
            20                  25                  30

Lys Ala Gln Pro Lys Val Glu Val Ile Glu Asp Glu Glu Leu Tyr Asn
        35                  40                  45

Cys Ala Lys Glu Ala Met Glu Ala Cys Pro Val Ser Ala Ile Thr Ile
    50                  55                  60

Glu Glu Ala Gly Gly Ser Ser Leu Val Pro Arg Gly Ser Glu Phe Met
65                  70                  75                  80

Gly Gln Ile His Gly Leu Ser Pro Thr Pro Ile Pro Lys Ala Pro Arg
                85                  90                  95

Gly Leu Ser Thr His His Trp Leu Asn Phe Leu Gln Ala Ala Tyr Arg
            100                 105                 110

Leu Gln Pro Arg Pro Ser Asp Phe Asp Phe Gln Gln Leu Arg Arg Phe
        115                 120                 125

Leu Lys Leu Ala Leu Lys Thr Pro Ile Trp Leu Asn Pro Ile Asp Tyr
    130                 135                 140

Ser Leu Leu Ala Ser Leu Ile Pro Lys Gly Tyr Pro Gly Arg Val Val
145                 150                 155                 160

Glu Ile Ile Asn Ile Leu Val Lys Asn Gln Val Ser Pro Ser Ala Pro
                165                 170                 175

Ala Ala Pro Val Pro Thr Pro Ile Cys Pro Thr Thr Thr Pro Pro Pro
            180                 185                 190

Pro Pro Pro Pro Ser Pro Glu Ala His Val Pro Pro Tyr Val Glu
```

```
              195                 200                 205
Pro Thr Thr Thr Gln Cys Phe
    210                 215

(2) INFORMATION FOR SEQ ID NO: 10:

(i) SEQUENCE CHARACTERISTICS:
        (A) LENGTH: 810 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: SYNTHESIZED, HTLV-I (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:10: FROM 1 TO 810

(xi) SEQUENCE DESCRIPTION: SEQ ID NO: 10:

ATGGCGTGGA AGGTTTCTGT CGACCAAGAC ACCTGTATAG GAGATGCCAT CTGTGCAAGC       60

CTCTGTCCAG ACGTCTTTGA GATGAACGAT GAAGGAAAGG CCCAACCAAA GGTAGAGGTT      120

ATTGAGGACG AAGAGCTCTA CAACTGTGCT AAGGAAGCTA TGGAGGCCTG TCCAGTTAGT      180

GCTATTACTA TTGAGGAGGC TGGTGGTTCT TCTCTGGTTC CGCGTGGATC GGAATTCGCA      240

GTACCGGTGG CGGTCTGGCT TGTCTCCGCC CTGGCCATGG GAGCCGGAGT GGCTGGCAGG      300

ATTACCGGCT CCATGTCCCT CGCCTCAGGA AAGAGCCTCC TACATGAGGT GGACAAAGAT      360

ATTTCCCAAT TAACTCAAGC AATAGTCAAA AACCACAAAA ATCTGCTCAA AATTGCACAG      420

TATGCTGCCC AGAACAGACG AGGCCTTGAT CTCCTGTTCT GGGAGCAAGG AGGATTATGC      480

AAAGCATTAC AAGAACAGTG CTGTTTTCTA AATATTACTA ATTCCCATGT CTCAATACTA      540

CAAGAGAGAC CCCCCCTTGA AAATCGAGTC CTGACTGGCT GGGGCCTTAA CTGGGACCTT      600

GGCCTCTCAC AGTGGGCTCG AGAAGCCTTA CAAACTGGAA TCACCCTTGT CGCGCTACTC      660

CTTCTTGTTA TCCTTGCAGG ACCATGCATC CTCCGTCAGC TACGACACCT CCCCTCGCGC      720

GTCAGATACC CCCATTACTC TCTTATAAAC CCTGAGTCAT CCCTGTAAGG ATCCGGGCCC      780

TCTAGATGCG GCCGCATGCA TGGTACCTAA                                      810

(2) INFORMATION FOR SEQ ID NO: 11:

(i) SEQUENCE CHARACTERISTICS:
        (A) LENGTH: 255 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:11: FROM 1 TO 255

(xi) SEQUENCE DESCRIPTION: SEQ ID NO: 11:
```

-continued

```
Met Ala Trp Lys Val Ser Val Asp Gln Asp Thr Cys Ile Gly Asp Ala
1               5                   10                  15

Ile Cys Ala Ser Leu Cys Pro Asp Val Phe Glu Met Asn Asp Glu Gly
                20                  25                  30

Lys Ala Gln Pro Lys Val Glu Val Ile Glu Asp Glu Glu Leu Tyr Asn
                35                  40                  45

Cys Ala Lys Glu Ala Met Glu Ala Cys Pro Val Ser Ala Ile Thr Ile
50                  55                  60

Glu Glu Ala Gly Gly Ser Ser Leu Val Pro Arg Gly Ser Glu Phe Ala
65                  70                  75                  80

Val Pro Val Ala Val Trp Leu Val Ser Ala Leu Ala Met Gly Ala Gly
                85                  90                  95

Val Ala Gly Arg Ile Thr Gly Ser Met Ser Leu Ala Ser Gly Lys Ser
                100                 105                 110

Leu Leu His Glu Val Asp Lys Asp Ile Ser Gln Leu Thr Gln Ala Ile
            115                 120                 125

Val Lys Asn His Lys Asn Leu Leu Lys Ile Ala Gln Tyr Ala Ala Gln
130                 135                 140

Asn Arg Arg Gly Leu Asp Leu Leu Phe Trp Glu Gln Gly Gly Leu Cys
145                 150                 155                 160

Lys Ala Leu Gln Glu Gln Cys Cys Phe Leu Asn Ile Thr Asn Ser His
                165                 170                 175

Val Ser Ile Leu Gln Glu Arg Pro Pro Leu Glu Asn Arg Val Leu Thr
                180                 185                 190

Gly Trp Gly Leu Asn Trp Asp Leu Gly Leu Ser Gln Trp Ala Arg Glu
            195                 200                 205

Ala Leu Gln Thr Gly Ile Thr Leu Val Ala Leu Leu Leu Leu Val Ile
210                 215                 220

Leu Ala Gly Pro Cys Ile Leu Arg Gln Leu Arg His Leu Pro Ser Arg
225                 230                 235                 240

Val Arg Tyr Pro His Tyr Ser Leu Ile Asn Pro Glu Ser Ser Leu
            245                 250                 255
```

(2) INFORMATION FOR SEQ ID NO: 12:

(i) SEQUENCE CHARACTERISTICS:
        (A) LENGTH: 816 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: SYNTHESIZED, HTLV-II (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:12: FROM 1 TO 816

(xi) SEQUENCE DESCRIPTION: SEQ ID NO: 12:

```
ATGGCGTGGA AGGTTTCTGT CGACCAAGAC ACCTGTATAG AGATGCCAT CTGTGCAAGC      60

CTCTGTCCAG ACGTCTTTGA GATGAACGAT GAAGGAAAGG CCCAACCAAA GGTAGAGGTT    120

ATTGAGGACG AAGAGCTCTA CAACTGTGCT AAGGAAGCTA TGGAGGCCTG TCCAGTTAGT    180

GCTATTACTA TTGAGGAGGC TGGTGGTTCT TCTCTGGTTC CGCGTGGATC GGAATTCGCC    240
```

```
GTTCCAATAG CAGTGTGGCT TGTCTCCGCC CTAGCGGCCG GAACAGGTAT CGCTGGTGGA      300

GTAACAGGCT CCCTATCTCT GGCTTCCAGT AAAAGCCTTC TCCTCGAGGT TGACAAAGAC      360

ATCTCCCACC TTACCCAGGC CATAGTCAAA AATCATCAAA ACATCCTCCG GGTTGCACAG      420

TATGCAGCCC AAAATAGACG AGGATTAGAC CTCCTATTCT GGGAACAAGG GGGTTTGTGC      480

AAGGCCATAC AGGAGCAATG TTGCTTCCTC AACATCAGTA ACACTCATGT ATCCGTCCTC      540

CAGGAACGGC CCCCTCTTGA AAAACGTGTC ATCACCGGCT GGGGACTAAA CTGGGATCTT      600

GGACTGTCCC AATGGGCACG AGAAGCCCTC CAGACAGGCA TAACCATTCT CGCTCTACTC      660

CTCCTCGTCA TATTGTTTGG CCCCTGTATC CTCCGCCAAA TCCAGGCCCT TCCACAGCGG      720

TTACAAAACC GACATAACCA GTATTCCCTT ATCAACCCAG AAACCATGCT ATAAGGATCC      780

GGGCCCTCTA GATGCGGCCG CATGCATGGT ACCTAA                               816
```

(2) INFORMATION FOR SEQ ID NO: 13:

(i) SEQUENCE CHARACTERISTICS:
        (A) LENGTH: 257 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:13: FROM 1 TO 257

(xi) SEQUENCE DESCRIPTION: SEQ ID NO: 13:

```
Met Ala Trp Lys Val Ser Val Asp Gln Asp Thr Cys Ile Gly Asp Ala
1               5                   10                  15

Ile Cys Ala Ser Leu Cys Pro Asp Val Phe Glu Met Asn Asp Glu Gly
            20                  25                  30

Lys Ala Gln Pro Lys Val Glu Val Ile Glu Asp Glu Glu Leu Tyr Asn
        35                  40                  45

Cys Ala Lys Glu Ala Met Glu Ala Cys Pro Val Ser Ala Ile Thr Ile
    50                  55                  60

Glu Glu Ala Gly Gly Ser Ser Leu Val Pro Arg Gly Ser Glu Phe Ala
65                  70                  75                  80

Val Pro Ile Ala Val Trp Leu Val Ser Ala Leu Ala Ala Gly Thr Gly
                85                  90                  95

Ile Ala Gly Gly Val Thr Gly Ser Leu Ser Leu Ala Ser Ser Lys Ser
            100                 105                 110

Leu Leu Leu Glu Val Asp Lys Asp Ile Ser His Leu Thr Gln Ala Ile
        115                 120                 125

Val Lys Asn His Gln Asn Ile Leu Arg Val Ala Gln Tyr Ala Ala Gln
    130                 135                 140

Asn Arg Arg Gly Leu Asp Leu Leu Phe Trp Glu Gln Gly Gly Leu Cys
145                 150                 155                 160

Lys Ala Ile Gln Glu Gln Cys Cys Phe Leu Asn Ile Ser Asn Thr His
                165                 170                 175

Val Ser Val Leu Gln Glu Arg Pro Pro Leu Glu Lys Arg Val Ile Thr
            180                 185                 190
```

```
Gly Trp Gly Leu Asn Trp Asp Leu Gly Leu Ser Gln Trp Ala Arg Glu
        195                 200                 205

Ala Leu Gln Thr Gly Ile Thr Ile Leu Ala Leu Leu Leu Val Ile
    210                 215                 220

Leu Phe Gly Pro Cys Ile Leu Arg Gln Ile Gln Ala Leu Pro Gln Arg
225                 230                 235                 240

Leu Gln Asn Arg His Asn Gln Tyr Ser Leu Ile Asn Pro Glu Thr Met
                245                 250                 255

Leu (2) INFORMATION FOR SEQ ID NO: 14:

(i) SEQUENCE CHARACTERISTICS:
        (A) LENGTH: 1119 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: PLASMID, Tp
        (B) STRAIN: NICHOLS (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:14: FROM 1 TO 1119

(xi) SEQUENCE DESCRIPTION: SEQ ID NO: 14:

ATGTCCCCTA TACTAGGTTA TTGGAAAATT AAGGGCCTTG TGCAACCCAC TCGACTTCTT      60

TTGGAATATC TTGAAGAAAA ATATGAAGAG CATTTGTATG AGCGCGATGA AGGTGATAAA     120

TGGCGAAACA AAAGTTTGA ATTGGGTTTG GAGTTTCCCA ATCTTCCTTA TTATATTGAT      180

GGTGATGTTA AATTAACACA GTCTATGGCC ATCATACGTT ATATAGCTGA CAAGCACAAC     240

ATGTTGGGTG TTGTCCAAA AGAGCGTGCA GAGATTTCAA TGCTTGAAGG AGCGGTTTTG      300

GATATTAGAT ACGGTGTTTC GAGAATTGCA TATAGTAAAG ACTTTGAAAC TCTCAAAGTT     360

GATTTTCTTA GCAAGCTACC TGAAATGCTG AAAATGTTCG AAGATCGTTT ATGTCATAAA     420

ACATATTTAA ATGGTGATCA TGTAACCCAT CCTGACTTCA TGTTGTATGA CGCTCTTGAT     480

GTTGTTTTAT ACATGGACCC AATGTGCCTG GATGCGTTCC CAAAATTAGT TTGTTTTAAA     540

AAACGTATTG AAGCTATCCC ACAAATTGAT AAGTACTTGA ATCCAGCAA GTATATAGCA     600

TGGCCTTTGC AGGGCTGGCA AGCCACGTTT GGTGGTGGCG ACCATCCTCC AAAATCGGAT     660

CTGGTTCCGC GTGGATCGGA ATTCTGTTCA TTTAGTTCTA TCCCGAATGG CACGTACCGG     720

GCGACGTATC AGGATTTTGA TGAGAATGGT TGGAAGGACT TTCTCGAGGT TACTTTTGAT     780

GGTGGCAAGA TGGTGCAGGT GGTTTACGAT TATCAGCATA AGAAGGGCG GTTTAAGTCC      840

CAGGACGCTG ACTACCATCG GGTCATGTAT GCATCCTCGG GCATAGGTCC TGAAAAGGCC     900

TTCAGAGAGC TCGCCGATGC TTTGCTTGAA AAGGGTAATC CCGAGATGGT GGATGTGGTC     960

ACCGGTGCAA CTGTTTCTTC CCAGAGTTTC AGGAGGTTGG GTCGTGCGCT TCTGCAGAGT    1020

GCGCGGCGCG CGAGAAGGA AGCCATTATT AGCAGGTAGG AATTCGTCGA CCTCGAGGGA    1080

TCCGGGCCCT CTAGATGCGG CCGCATGCAT GGTACCTAA                            1119

(2) INFORMATION FOR SEQ ID NO: 15:
```

```
    (i) SEQUENCE CHARACTERISTICS:
        (A) LENGTH: 352 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:15: FROM 1 TO 352

(xi) SEQUENCE DESCRIPTION: SEQ ID NO: 15:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
210                 215                 220

Gly Ser Glu Phe Cys Ser Phe Ser Ser Ile Pro Asn Gly Thr Tyr Arg
225                 230                 235                 240

Ala Thr Tyr Gln Asp Phe Asp Glu Asn Gly Trp Lys Asp Phe Leu Glu
                245                 250                 255

Val Thr Phe Asp Gly Gly Lys Met Val Gln Val Val Tyr Asp Tyr Gln
                260                 265                 270

His Lys Glu Gly Arg Phe Lys Ser Gln Asp Ala Asp Tyr His Arg Val
            275                 280                 285

Met Tyr Ala Ser Ser Gly Ile Gly Pro Glu Lys Ala Phe Arg Glu Leu
            290                 295                 300

Ala Asp Ala Leu Leu Glu Lys Gly Asn Pro Glu Met Val Asp Val Val
305                 310                 315                 320
```

```
Thr Gly Ala Thr Val Ser Ser Gln Ser Phe Arg Arg Leu Gly Arg Ala
                325                 330                 335

Leu Leu Gln Ser Ala Arg Arg Gly Glu Lys Glu Ala Ile Ile Ser Arg
            340                 345                 350
```

(2) INFORMATION FOR SEQ ID NO: 16:

(i) SEQUENCE CHARACTERISTICS:
        (A) LENGTH: 858 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: E. COLI, Tp
        (B) STRAIN: DH15A, NICHOLS (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:16: FROM 1 TO 858

(xi) SEQUENCE DESCRIPTION: SEQ ID NO: 16:

```
ATGTTACACC AACAACGAAA CCAACACGCC AGGCTTATTC CTGTGGAGTT ATATATGAGC    60

GATAAAATTA TTCACCTGAC TGACGACAGT TTTGACACGG ATGTACTCAA AGCGGACGGG   120

GCGATCCTCG TCGATTTCTG GGCAGAGTGG TGCGGTCCGT GCAAAATGAT CGCCCCGATT   180

CTGGATGAAA TCGCTGACGA ATATCAGGGC AAACTGACCG TTGCAAAACT GAACATCGAT   240

CAAAACCCTG GCACTGCGCC GAAATATGGC ATCCGTGGTA TCCCGACTCT GCTGCTGTTC   300

AAAAACGGTG AAGTGGCGGC AACCAAAGTG GGTGCACTGT CTAAAGGTCA GTTGAAAGAG   360

TTCCTCGACG CTAACCTGGC GGAGCTCGGT GGTTCTTCTC TGGTTCCGCG TGGATCGGAA   420

TTCTGTTCAT TTAGTTCTAT CCCGAATGGC ACGTACCGGG CGACGTATCA GGATTTTGAT   480

GAGAATGGTT GGAAGGACTT TCTCGAGGTT ACTTTTGATG GTGGCAAGAT GGTGCAGGTG   540

GTTTACGATT ATCAGCATAA AGAAGGGCGG TTTAAGTCCC AGGACGCTGA CTACCATCGG   600

GTCATGTATG CATCCTCGGG CATAGGTCCT GAAAAGGCCT TCAGAGAGCT CGCCGATGCT   660

TTGCTTGAAA AGGGTAATCC CGAGATGGTG GATGTGGTCA CCGGTGCAAC TGTTTCTTCC   720

CAGAGTTTCA GGAGGTTGGG TCGTGCGCTT CTGCAGAGTG CGCGGCGCGG CGAGAAGGAA   780

GCCATTATTA GCAGGTAGGA ATTCGTCGAC CTCGAGGGAT CCGGGCCCTC TAGATGCGGC   840

CGCATGCATG GTACCTAA                                                 858
```

(2) INFORMATION FOR SEQ ID NO: 17:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF EXPRESSING SAID FUSED PROTEIN
(K) RELEVANT RESIDUES IN SEQ ID NO:17: FROM 1 TO 265

(xi) SEQUENCE DESCRIPTION: SEQ ID NO: 17:

```
Met Leu His Gln Gln Arg Asn Gln His Ala Arg Leu Ile Pro Val Glu
1               5                   10                  15

Leu Tyr Met Ser Asp Lys Ile Ile His Leu Thr Asp Asp Ser Phe Asp
            20                  25                  30

Thr Asp Val Leu Lys Ala Asp Gly Ala Ile Leu Val Asp Phe Trp Ala
            35                  40                  45

Glu Trp Cys Gly Pro Cys Lys Met Ile Ala Pro Ile Leu Asp Glu Ile
50                      55                  60

Ala Asp Glu Tyr Gln Gly Lys Leu Thr Val Ala Lys Leu Asn Ile Asp
65                  70                  75                  80

Gln Asn Pro Gly Thr Ala Pro Lys Tyr Gly Ile Arg Gly Ile Pro Thr
                85                  90                  95

Leu Leu Leu Phe Lys Asn Gly Glu Val Ala Ala Thr Lys Val Gly Ala
                100                 105                 110

Leu Ser Lys Gly Gln Leu Lys Glu Phe Leu Asp Ala Asn Leu Ala Glu
            115                 120                 125

Leu Gly Gly Ser Ser Leu Val Pro Arg Gly Ser Glu Phe Cys Ser Phe
            130                 135                 140

Ser Ser Ile Pro Asn Gly Thr Tyr Arg Ala Thr Tyr Gln Asp Phe Asp
145                 150                 155                 160

Glu Asn Gly Trp Lys Asp Phe Leu Glu Val Thr Phe Asp Gly Gly Lys
                165                 170                 175

Met Val Gln Val Val Tyr Asp Tyr Gln His Lys Glu Gly Arg Phe Lys
                180                 185                 190

Ser Gln Asp Ala Asp Tyr His Arg Val Met Tyr Ala Ser Ser Gly Ile
            195                 200                 205

Gly Pro Glu Lys Ala Phe Arg Glu Leu Ala Asp Ala Leu Leu Glu Lys
            210                 215                 220

Gly Asn Pro Glu Met Val Asp Val Val Thr Gly Ala Thr Val Ser Ser
225                 230                 235                 240

Gln Ser Phe Arg Arg Leu Gly Arg Ala Leu Leu Gln Ser Ala Arg Arg
                245                 250                 255

Gly Glu Lys Glu Ala Ile Ile Ser Arg
                260                 265
```

(2) INFORMATION FOR SEQ ID NO: 18:

(i) SEQUENCE CHARACTERISTICS:
      (A) LENGTH: 672 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: SYNTHESIZED, Tp
      (B) STRAIN: NICHOLS (x) PUBLICATION INFORMATION:
      (A) AUTHORS: NOBUYUKI FUJII ET AL,
      (B) TITLE: FUSED DNA SEQUENCE, FUSED PROTEIN EXPRESSED
         FROM SAID FUSED DNA SEQUENCE AND METHOD OF
         EXPRESSING SAID FUSED PROTEIN
      (K) RELEVANT RESIDUES IN SEQ ID NO:18: FROM 1 TO 672

(xi) SEQUENCE DESCRIPTION: SEQ ID NO: 18:

```
ATGGCGTGGA AGGTTTCTGT CGACCAAGAC ACCTGTATAG GAGATGCCAT CTGTGCAAGC    60

CTCTGTCCAG ACGTCTTTGA GATGAACGAT GAAGGAAAGG CCCAACCAAA GGTAGAGGTT   120

ATTGAGGACG AAGAGCTCTA CAACTGTGCT AAGGAAGCTA TGGAGGCCTG TCCAGTTAGT   180

GCTATTACTA TTGAGGAGGC TGGTGGTTCT TCTCTGGTTC CGCGTGGATC GGAATTCTGT   240

TCATTTAGTT CTATCCCGAA TGGCACGTAC CGGGCGACGT ATCAGGATTT TGATGAGAAT   300

GGTTGGAAGG ACTTTCTCGA GGTTACTTTT GATGGTGGCA AGATGGTGCA GGTGGTTTAC   360

GATTATCAGC ATAAAGAAGG GCGGTTTAAG TCCCAGGACG CTGACTACCA TCGGGTCATG   420

TATGCATCCT CGGGCATAGG TCCTGAAAAG GCCTTCAGAG AGCTCGCCGA TGCTTTGCTT   480

GAAAAGGGTA ATCCCGAGAT GGTGGATGTG GTCACCGGTG CAACTGTTTC TTCCCAGAGT   540

TTCAGGAGGT TGGGTCGTGC GCTTCTGCAG AGTGCGCGGC GCGGCGAGAA GGAAGCCATT   600

ATTAGCAGGT AGGAATTCGT CGACCTCGAG GGATCCGGGC CCTCTAGATG CGGCCGCATG   660

CATGGTACCT AA                                                      672
```

(2) INFORMATION FOR SEQ ID NO: 19:

(i) SEQUENCE CHARACTERISTICS:
        (A) LENGTH: 203 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: RECOMBINANT (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN
        (K) RELEVANT RESIDUES IN SEQ ID NO:19: FROM 1 TO 203

(xi) SEQUENCE DESCRIPTION: SEQ ID NO: 19:

```
Met Ala Trp Lys Val Ser Val Asp Gln Asp Thr Cys Ile Gly Asp Ala
1               5                   10                  15

Ile Cys Ala Ser Leu Cys Pro Asp Val Phe Glu Met Asn Asp Glu Gly
            20                  25                  30

Lys Ala Gln Pro Lys Val Glu Val Ile Glu Asp Glu Glu Leu Tyr Asn
        35                  40                  45

Cys Ala Lys Glu Ala Met Glu Ala Cys Pro Val Ser Ala Ile Thr Ile
    50                  55                  60

Glu Glu Ala Gly Gly Ser Ser Leu Val Pro Arg Gly Ser Glu Phe Cys
65                  70                  75                  80

Ser Phe Ser Ser Ile Pro Asn Gly Thr Tyr Arg Ala Thr Tyr Gln Asp
                85                  90                  95

Phe Asp Glu Asn Gly Trp Lys Asp Phe Leu Glu Val Thr Phe Asp Gly
            100                 105                 110

Gly Lys Met Val Gln Val Val Tyr Asp Tyr Gln His Lys Glu Gly Arg
        115                 120                 125

Phe Lys Ser Gln Asp Ala Asp Tyr His Arg Val Met Tyr Ala Ser Ser
    130                 135                 140

Gly Ile Gly Pro Glu Lys Ala Phe Arg Glu Leu Ala Asp Ala Leu Leu
145                 150                 155                 160

Glu Lys Gly Asn Pro Glu Met Val Asp Val Val Thr Gly Ala Thr Val
```

```
                    165                 170                 175
Ser Ser Gln Ser Phe Arg Arg Leu Gly Arg Ala Leu Leu Gln Ser Ala
            180                 185                 190

Arg Arg Gly Glu Lys Glu Ala Ile Ile Ser Arg
        195                 200
```

(2) INFORMATION FOR SEQ ID NO: 20:

(i) SEQUENCE CHARACTERISTICS:
        (A) LENGTH: 1035 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: SYNTHESIZED, Tp
        (B) STRAIN: NICHOLS (x) PUBLICATION INFORMATION:
        (A) AUTHORS: NOBUYUKI FUJII ET AL,
        (B) TITLE: FUSED DNA SEQUENCE, FUSED PROTEIN EXPRESSED
            FROM SAID FUSED DNA SEQUENCE AND METHOD OF
            EXPRESSING SAID FUSED PROTEIN (xi) SEQUENCE DESCRIPTION: SEQ ID NO: 20:

```
ATGAAGATTG GTATTGTAAC TGGTATCCCT GGTGTAGGGA AAAGTACTGT CTTGGCTAAA     60

GTTAAAGAGA TATTGGATAA TCAAGGTATA AATAACAAGA TCATAAATTA TGGAGATTTT    120

ATGTTAGCAA CAGCATTAAA ATTAGGCTAT GCTAAAGATA GAGACGAAAT GAGAAAATTA    180

TCTGTAGAAA AGCAGAAGAA ATTGCAGATT GATGCGGCTA AAGGTATAGC TGAAGAGGCA    240

AGAGCAGGTG GAGAAGGATA TCTGTTCATA GATACGCACG CTGTGATACG TACACCCTCT    300

GGATATTTAC TGGTTTACC GTCAGATATA ATTACAGAAA TAAATCCGTC TGTTATCTTT     360

TTACTGGAAG CTGATCCTAA GATAATATTA TCAAGGCAAA AGAGAGATAC AACAAGGAAT    420

AGAAATGATT ATAGTGACGA ATCAGTTATA TTAGAAACCA TAAACTTCGC TAGATATGCA    480

GCTACTGCTT CTGCAGTATT AGCCGGTTCT ACTGTTAAGG TAATTGTAAA CGTGGAAGGA    540

GATCCTAGTA TAGCAGCTAA TGAGATAATA AGGTCTATGA AGGGTGGTTC TTCTCTGGTT    600

CCGCGTGGAT CGGAATTCTG TTCATTTAGT TCTATCCCGA ATGGCACGTA CCGGGCGACG    660

TATCAGGATT TTGATGAGAA TGGTTGGAAG GACTTTCTCG AGGTTACTTT TGATGGTGGC    720

AAGATGGTGC AGGTGGTTTA CGATTATCAG CATAAAGAAG GCGGTTTAA GTCCCAGGAC     780

GCTGACTACC ATCGGGTCAT GTATGCATCC TCGGGCATAG GTCCTGAAAA GGCCTTCAGA    840

GAGCTCGCCG ATGCTTTGCT TGAAAAGGGT AATCCCGAGA TGGTGGATGT GGTCACCGGT    900

GCAACTGTTT CTTCCCAGAG TTTCAGGAGG TTGGGTCGTG CGCTTCTGCA GAGTGCGCGG    960

CGCGGCGAGA AGGAAGCCAT TATTAGCAGG TAGGGATCCG GGCCCTCTAG ATGCGGCCGC   1020

ATGCATGGTA CCTAA                                                   1035
```

(2) INFORMATION FOR SEQ ID NO: 21:

(i) SEQUENCE CHARACTERISTICS:
        (A) LENGTH: 330 amino acids
        (B) TYPE: amino acid
        (C) STRANDEDNESS: single
        (D) TOPOLOGY: linear (ii) MOLECULE TYPE: protein (vi) ORIGINAL SOURCE:

-continued (A) ORGANISM: RECOMBINANT (x) PUBLICATION INFORMATION:
    (A) AUTHORS: NOBUYUKI FUJII ET AL,
    (B) TITLE: FUSED DNA SEQUENCE, FUSED PROTEIN EXPRESSED
        FROM SAID FUSED DNA SEQUENCE AND METHOD OF
        EXPRESSING SAID FUSED PROTEIN
    (K) RELEVANT RESIDUES IN SEQ ID NO:21: FROM 1 TO 330

(xi) SEQUENCE DESCRIPTION: SEQ ID NO: 21:

```
Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30

Lys Ile Ile Asn Tyr Gly Asp Phe Met Leu Ala Thr Ala Leu Lys Leu
            35                  40                  45

Gly Tyr Ala Lys Asp Arg Asp Glu Met Arg Lys Leu Ser Val Glu Lys
        50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Asp Ile Ile Thr
                100                 105                 110

Glu Ile Asn Pro Ser Val Ile Phe Leu Leu Glu Ala Asp Pro Lys Ile
                115                 120                 125

Ile Leu Ser Arg Gln Lys Arg Asp Thr Thr Arg Asn Arg Asn Asp Tyr
130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
                180                 185                 190

Met Lys Gly Gly Ser Ser Leu Val Pro Arg Gly Ser Glu Phe Cys Ser
                195                 200                 205

Phe Ser Ser Ile Pro Asn Gly Thr Tyr Arg Ala Thr Tyr Gln Asp Phe
210                 215                 220

Asp Glu Asn Gly Trp Lys Asp Phe Leu Glu Val Thr Phe Asp Gly Gly
225                 230                 235                 240

Lys Met Val Gln Val Val Tyr Asp Tyr Gln His Lys Glu Gly Arg Phe
                245                 250                 255

Lys Ser Gln Asp Ala Asp Tyr His Arg Val Met Tyr Ala Ser Ser Gly
                260                 265                 270

Ile Gly Pro Glu Lys Ala Phe Arg Glu Leu Ala Asp Ala Leu Leu Glu
                275                 280                 285

Lys Gly Asn Pro Glu Met Val Asp Val Val Thr Gly Ala Thr Val Ser
                290                 295                 300

Ser Gln Ser Phe Arg Arg Leu Gly Arg Ala Leu Leu Gln Ser Ala Arg
305                 310                 315                 320

Arg Gly Glu Lys Glu Ala Ile Ile Ser Arg
                325                 330
```